(12) United States Patent
Panicker et al.

(10) Patent No.: US 9,933,367 B2
(45) Date of Patent: Apr. 3, 2018

(54) METHOD TO IDENTIFY AND ISOLATE PLURIPOTENT STEM CELLS USING ENDOGENOUS BLUE FLUORESCENCE

(71) Applicant: NATIONAL CENTRE FOR BIOLOGICAL SCIENCES, Bangalore, Karnataka (IN)

(72) Inventors: Mitradas M. Panicker, Bangalore (IN); Radhika Menon, Bangalore (IN); Muthusamy Thangaselvam, Bangalore (IN); Odity Mukherjee, Bangalore (IN)

(73) Assignee: NATIONAL CENTRE FOR BIOLOGICAL SCIENCES, Bangalore, Karnataka (IN)

( * ) Notice: Subject to any disclaimer, the term of this patent is extended or adjusted under 35 U.S.C. 154(b) by 381 days.

(21) Appl. No.: 14/442,226

(22) PCT Filed: Nov. 12, 2013

(86) PCT No.: PCT/IB2013/060076
§ 371 (c)(1),
(2) Date: May 12, 2015

(87) PCT Pub. No.: WO2014/072960
PCT Pub. Date: May 15, 2014

(65) Prior Publication Data
US 2016/0305885 A1  Oct. 20, 2016

(30) Foreign Application Priority Data
Nov. 12, 2012 (IN) ............................ 4743/CHE/2012

(51) Int. Cl.
| | |
|---|---|
| *C12N 5/02* | (2006.01) |
| *C12N 5/00* | (2006.01) |
| *G01N 21/64* | (2006.01) |
| *C12N 5/0735* | (2010.01) |
| *C12N 5/074* | (2010.01) |
| *C12Q 1/04* | (2006.01) |

(52) U.S. Cl.
CPC ....... *G01N 21/6486* (2013.01); *C12N 5/0606* (2013.01); *C12N 5/0696* (2013.01); *C12Q 1/04* (2013.01); *C12N 2501/115* (2013.01); *C12N 2501/16* (2013.01); *C12N 2501/2306* (2013.01); *C12N 2501/727* (2013.01)

(58) Field of Classification Search
CPC .............. G01N 21/6486; C12N 5/0606; C12N 5/0696; C12N 1/04; C12N 2501/115; C12N 2501/16; C12N 2501/2306; C12N 2501/727

IPC ................................................ C12N 5/02,5/00
See application file for complete search history.

(56) References Cited

U.S. PATENT DOCUMENTS

| | | |
|---|---|---|
| 2011/0151447 A1 | 6/2011 | Park et al. |
| 2012/0276578 A1 | 11/2012 | Stringari et al. |

FOREIGN PATENT DOCUMENTS

| | | |
|---|---|---|
| WO | WO-96/39489 A1 | 12/1996 |

OTHER PUBLICATIONS

Cao et al. J. of Exp. Zoo., 311A: 368-376, 2009.*
Brevini et al. Theriogenology, 74: 544-550, 2010.*
Paris et al. Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Delphine Debarre et al.; Imaging Lipid Bodies in Cells and Tissues Using Third-Harmonic Generation Microscopy; Nature Methods, vol. 3, No. 1, p. 47-53, Jan. 2006.
Christoph Thiele et al.; Cell Biology of Lipid Droplets; Current Opinion in Cell Biology 2008, vol. 20, p. 378-385.
Valamehr et al., A novel platform to enable the high-throughput derication and characterization of feeder-free human iPSCs. Scientific Reports, 2012 (published online Jan. 6, 2012), vol. 2, p. 213, Especially abstract; p. 9, col. 2, para 3.
Zipfel et al., Live tissue intrinsic emission microscopy using multiphoton-excited native fluorescence and second harmonic generation. Proc Nat Acad Sci, Jun. 10, 2003, vol. 100, No. 12, pp. 7075-7080. Especially abstract; p. 7075, col. 2, para 2; p. 7076, col. 2, para 2-3.
Patalay et al. Quantification of cellular autofluorescence of human skin using multiphoton tomography and fluorescence lifetime imaging in two spectral detection channels. Biomed Opt Express, Dec. 1, 2011, vol. 2, No. 12, pp. 3295-3308. Entire document.

* cited by examiner

*Primary Examiner* — Thaian N Ton
(74) *Attorney, Agent, or Firm* — Harness, Dickey & Pierce, P.L.C.

(57) ABSTRACT

The instant disclosure provides for a method of identifying and isolating pluripotent stem cells and distinguishing pluripotent stem cells from differentiating/differentiated cells, using the property of endogenous blue fluorescence emitted from intracellular lipid bodies which serves as an endogenous marker for the pluripotent state.

10 Claims, 12 Drawing Sheets

Figure 1:
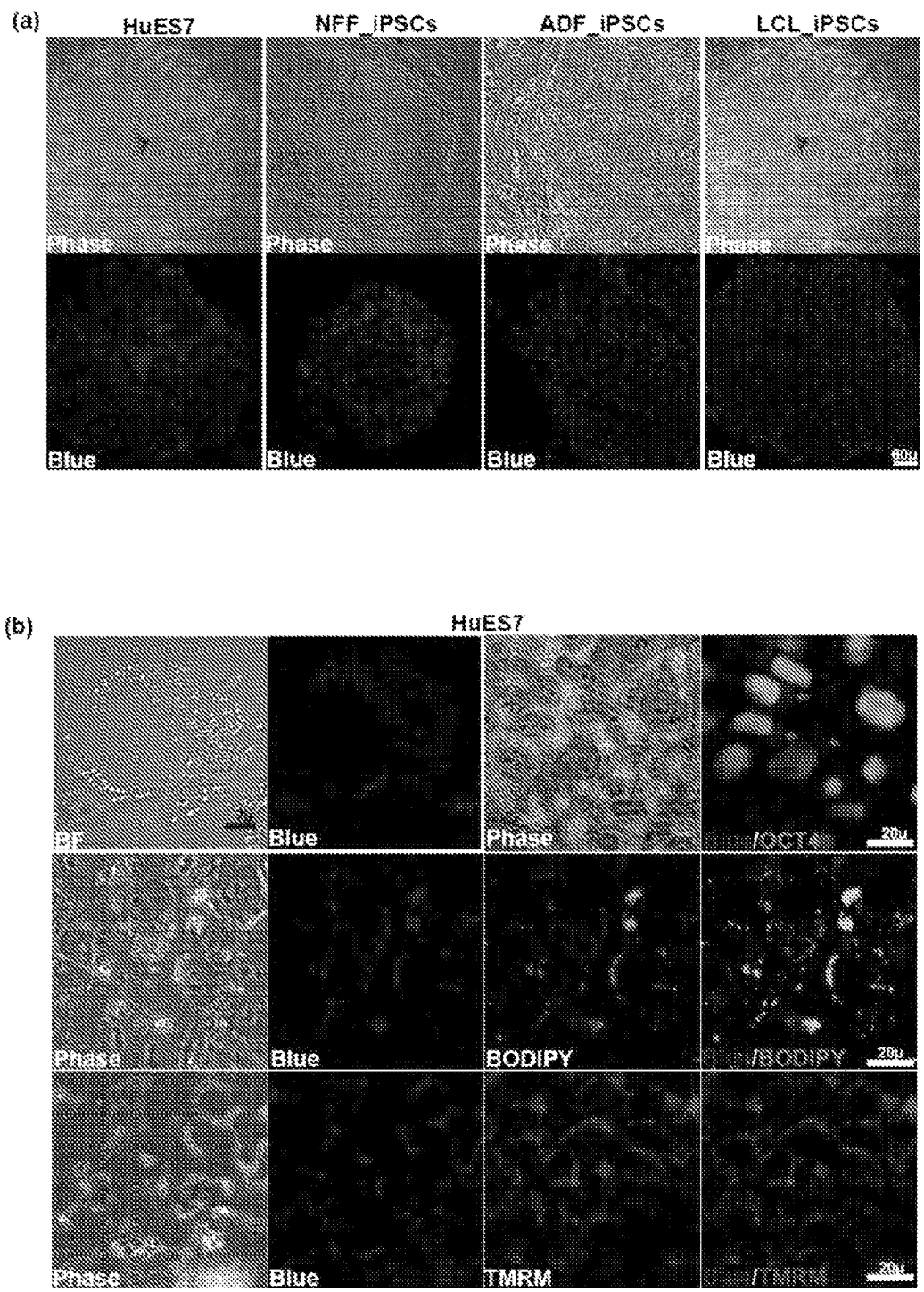

METHOD TO IDENTIFY AND ISOLATE PLURIPOTENT STEM CELLS USING ENDOGENOUS BLUE FLUORESCENCE

CROSS-REFERENCE TO RELATED APPLICATIONS

This application is a 371 U.S. National Stage of International Application No. PCT/IB2013/060076, filed Nov. 12, 2013, which claims the benefit of and priority to Indian Patent Application No. 4743/CHE/2012, filed Nov. 12, 2012. The entire disclosures of the above applications are incorporated herein by reference.

TECHNICAL FIELD

The present disclosure relates to identifying and isolating pluripotent stem cells, using endogenous blue fluorescence emission from lipid bodies. The pluripotent cells include human embryonic stem cells (HuES), human induced pluripotent stem cells (HiPSCs), mammalian stem cells as well as mouse epiblast (mEpiSCs) pluripotent stem cells. The instant method is a label-free method to identify and isolate primed pluripotent stem cells from differentiating/differentiated cells in a culture using the property of endogenous blue fluorescence emitted from intracellular lipid bodies, which serve as endogenous label free marker specific to human pluripotent stem cells (embryonic and induced) and mouse epiblast pluripotent stem cells. The instant disclosure provides for a method of validating the presence of pluripotent stem cells by carrying out conversion of human somatic cells to induced pluripotent stem cells; and also mouse embryonic stem cells and somatic cells to mouse epiblast (mEpiSCs) pluripotent stem cells. The instant disclosure also relates to using the lipid bodies as an endogenous marker for 'epiblast'-specific pluripotent stem cells in human and mouse.

BACKGROUND AND PRIOR ART OF THE DISCLOSURE

Current methods to isolate/identify live human embryonic and induced pluripotent stem cells or to monitor the process of reprogramming somatic cells, use antibodies against surface markers e.g. SSEA-4, SSEA-3, Tra-160, Tra-181 or have the cells genetically modified to report the expression of pluripotency genes, such as Oct-4 or Sox-2. Use of antibodies is subject to variability and/or genetic modification has obvious inherent safety issues if these cells are to be used in therapy later on. Other methods have used colony morphology or nuclear to cytoplasmic ratio, though this method is not definitive i.e. is only suggestive. For e.g. colony morphology does not address single cell isolation and has a strong subjective component. Conversely these methods are used to isolate differentiated cells away from teratoma-initiating pluripotent cells. A major thrust of human ES and iPS cells will be to generate specific differentiated cell types from pluripotent cells. Since these conversions are rarely complete, it would be important to eliminate the pluripotent cells within the differentiated population of cells. The pluripotent cells, if present, can differentiate to either to cells that are not desired or to tumor forming cells i.e. teratomas, which can interfere in the therapeutic use and in addition increase the possibility of malignant and benign tumors. The endogenous blue fluorescence can be used to isolate undifferentiated pluripotent cells from the differentiated cells.

A recent report had used fluorescence life-time measurements (FLIM) of endogenous fluorophores to discriminate between pluripotent and differentiating human embryonic stem cells using a custom-designed multiphoton microscope, fluorescence lifetime measurements along with phasor analysis. They reported that the fluorescence in the blue region emanating from pluripotent cells arose from two entities—NADH and LDAG (lipid droplet associated granules). LDAG are aggregates of lipid bodies, which are a mixture of neutral lipids contained by a monolayer of phospholipids and may also be associated with some proteins. The composition of lipids and proteins present in these bodies can vary within the cells and also between cells. They also state that the ratio of the levels of NADH fluorescence to the fluorescence emanating from lipid aggregates termed) within these cells are used to identify pluripotent human embryonic stem cells. The document used a multiphoton excitation source to measure the fluorescence lifetimes, subjected the intensities measured to phasor analysis to determine individual fluorescence lifetimes. These were stated to be plotted as a phasor plot to identify the sources and characteristics of the emitted fluorescence and estimate the differentiation of the pluripotent cell population. The method used a custom-designed FLIM microscope along with phasor analysis. The paper also emphasizes in multiple places that the relative ratio of the LDAG fluorescence to NADH fluorescence is used to determine the undifferentiated status. The report also did not demonstrate isolation/separation of pluripotent human cells from their differentiating counterparts. The above method has also not been applied to human induced pluripotent stem cells, mouse embryonic stem cells or mouse epiblast stem cells (mEpiSCs). The document also states that the fluorescence seen in the LDAG emanated from the reaction of lipid peroxides with proteins. The lipid peroxides are multiple chemical entities which are generated by the oxidation of lipids within the lipid bodies by reactive oxygen species (ROS), depending on the type of lipid molecules that are present. In particular, lipids that are unsaturated are more prone to oxidation. The document (Chiari et al.) did not identify or isolate any specific lipid or its oxidation product but speculated this to be so. It also stated that human ES cells have high ROS values compared to other cells and hence these bodies (LDAG) are fluorescent in human embryonic stem cells. However, there are various other literatures which indicate that ROS values in embryonic stem cells are lower than in differentiated cells.

The prior art document as aforementioned used a custom-designed FLIM microscope, not easily available, is expensive and technically challenging (for e.g. requires a femtosecond laser for excitation and requires measurement and separation of individual fluorescence lifetimes) and does not lend to FACS sorting. This technique is not suited for high throughput and cannot be compared favourably to sorting by FACS. The report also did not demonstrate physical isolation of pluripotent stem cells and subsequent culture of these cells or examined induced pluripotent stem cells or epiblast-like stem cells. The images provided by the FLIM microscope do not lend to easy mechanical dissection due to their low resolution. The method also depends on the fluorescence lifetimes of the fluorophores which are affected by the molecular environment in which the fluorophores reside and can show substantial variation and is highly context-dependent. For e.g., a master's thesis from the same laboratory had previously reported FLIM analysis of human embryonic stem cells and given a different interpretation/identification to the fluorescence observed. The paper also does not report the absence of lipid bodies and associated fluorescence in mouse ES cells, does not report any experiments with human induced pluripotent cells, and also does not associate the endogenous blue fluorescent lipid bodies with the epiblast-like stem cell state.

The instant disclosure overcomes the drawbacks in the prior art by describing a method which measures just the intensity of the endogenous blue fluorescence (i.e. autofluorescence) using standard wide-field epifluorescence microscopes to identify pluripotent stem cells. In addition it shows that conventional fluorescence activated cell sorting (FACS) is used to isolate pluripotent cells from differentiating cells again based on just the intensity of blue fluorescence. In other words, it does not require the measurement of fluorescence lifetimes and their analysis or the need to measure the ratio of LDAG fluorescence and NADH fluorescence to identify and isolate pluripotent cells. The instant disclosure also therefore easily lends itself to high throughput identification and isolation, for e.g. FACS, and subsequent propagation of human pluripotent stem cells unlike the FLIM method. The instant method also further demonstrates its application in isolating single human pluripotent stem cells (i.e. FACS is dependent on dispersion into single cells) and subsequent propagation, which has been a serious limitation in the prior art. This method also avoids the variability associated with antibody labeling or genetic modification.

The method described in the instant disclosure, in addition to examining the above, is robust can be easily and directly applied with standard equipment available in most laboratories and does not require specific expertise or training or very sophisticated instruments. Hence, the instant disclosure overcomes all the drawbacks presently being faced in the prior art and improves the current field of technology.

STATEMENT OF THE PRESENT DISCLOSURE

Accordingly, the present disclosure relates to a method for identifying pluripotent stem cell in a culture and optionally isolating the pluripotent stem cell from the culture, said method comprising acts of: a) subjecting the culture to excitation at wavelength ranging from about 275 nm to about 410 nm for obtaining endogenous blue fluorescence emission from lipid body present within the pluripotent stem cell; and b) measuring intensity of the emission for identifying the pluripotent stem cell in the culture; c) optionally sorting the culture for isolating the pluripotent stem cell from the culture.

BRIEF DESCRIPTION OF ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein:

BF—Bright field; HPSC: Human pluripotent stem cell; HuES: Human embryonic stem cell; HiPSC: Human induced pluripotent stem cell; NFF: Neonatal foreskin fibroblast; mEpiSC: mouse epiblast-like stem cell; NFF iPSC: Neonatal foreskin fibroblast induced pluripotent stem cell; ADF: Adult dermal fibroblast; ADF iPSC: Adult dermal fibroblast induced pluripotent stem cell; LCL: Lymphoblastoid cell line; LCL iPSC: Lymphoblastoid cell line induced pluripotent stem cell;

FIG. 1 shows that human pluripotent stem cells have cytoplasmic lipid bodies that have a characteristic blue fluorescence.

(a) Blue fluorescence (excitation—325-375 nm and emission—460-500 nm) was observed in all HuES and HiPS (NFF iPS, ADF iPS, LCL iPS) colonies cultured in typical media and culture conditions. (b) Representative high magnification images of HuES7 cells showing blue fluorescence confined to cytoplasmic spherical bodies (top left panel); these fluorescent spherical bodies often show polarized distribution within cells (red arrows—top right panel), are stained by the lipid body-specific marker BODIPY®493/503 (middle panel) and do not co-localize with the mitochondria-specific dye TMRM (lower panel) Confocal image (top left panel) was acquired at excitation—405 nm and emission—420-490 nm. BF—Bright field; NFF: Neonatal foreskin fibroblast ADF: Adult dermal fibroblast; LCL: Lymphoblastoid cell line; TMRM: Tetramethylrhodamine methyl ester.

Figure 2:
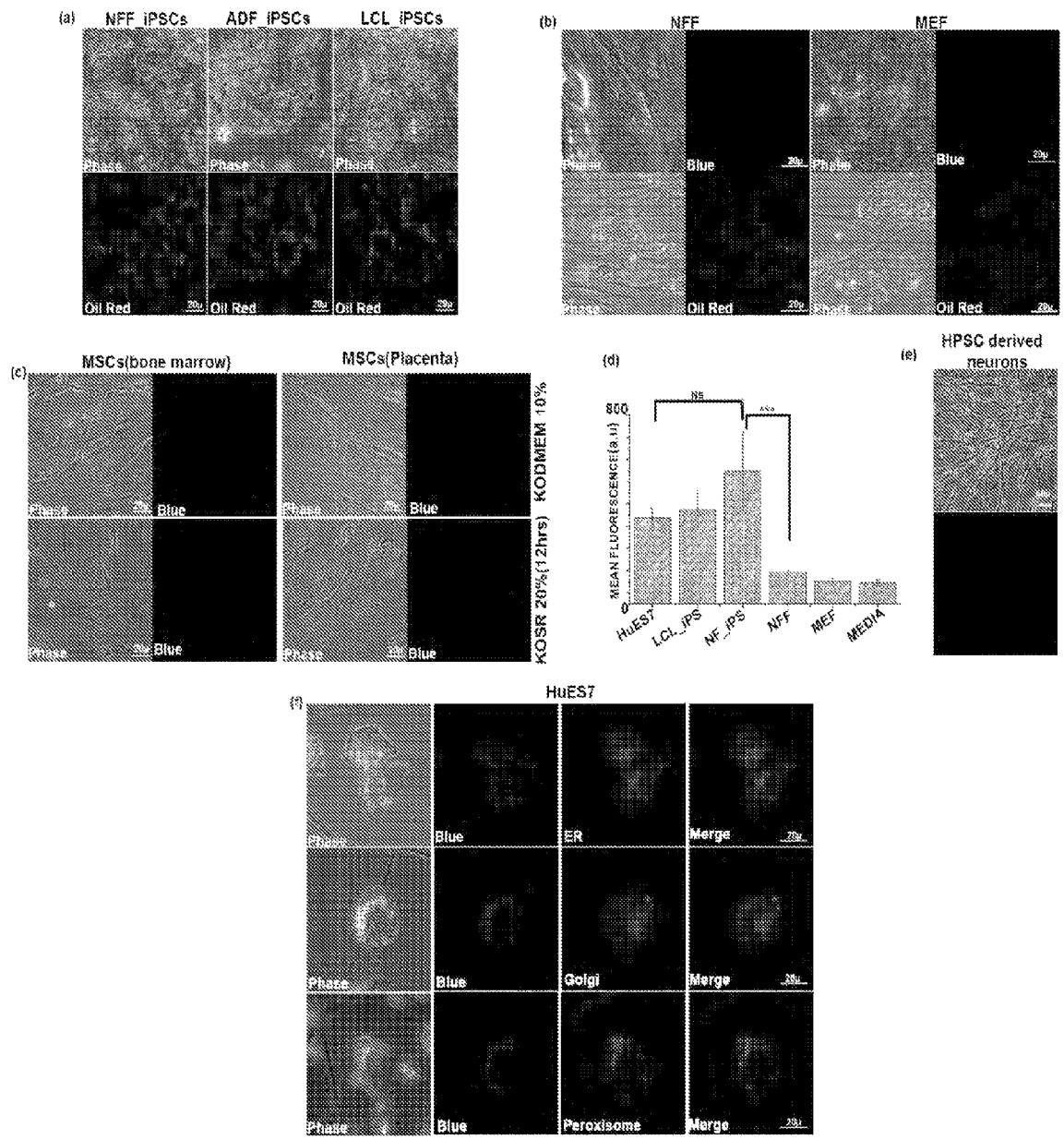

FIG. 2 shows that blue fluorescent lipid bodies are only present in HPSCs, not present in human somatic cells and excluded from other cytoplasmic (ER, Golgi and peroxisomes) organelles.

(a) HPSC cultures (HuES7, NFF iPSCs, ADF iPSCs and LCL iPSCs) show numerous lipid bodies (positive Oil Red O staining) (b) Oil Red O positive lipid bodies in human neonatal (NFF) and mouse embryonic (MEF) fibroblasts do not exhibit blue fluorescence and are not as prominent as in HPSCs. (c) Mesenchymal stem cells (MSCs) derived from human bone marrow and placenta do not exhibit blue fluorescence. (d) The blue fluorescence is significantly higher in HPSCs cultures compared to somatic cells. Mean fluorescence intensities are in arbitrary units (n=3, multiple colonies from three independent cultures for each cell type). (e) Neurons derived from HuES7 do not exhibit blue fluorescence. (f) The blue fluorescent lipid bodies present in HuES7 do not co-localize with endoplasmic reticulum, (ER—upper panel), Golgi apparatus (middle panel) or peroxisomes (lower panel). Significance level *** is <0.001.

Figure 3:
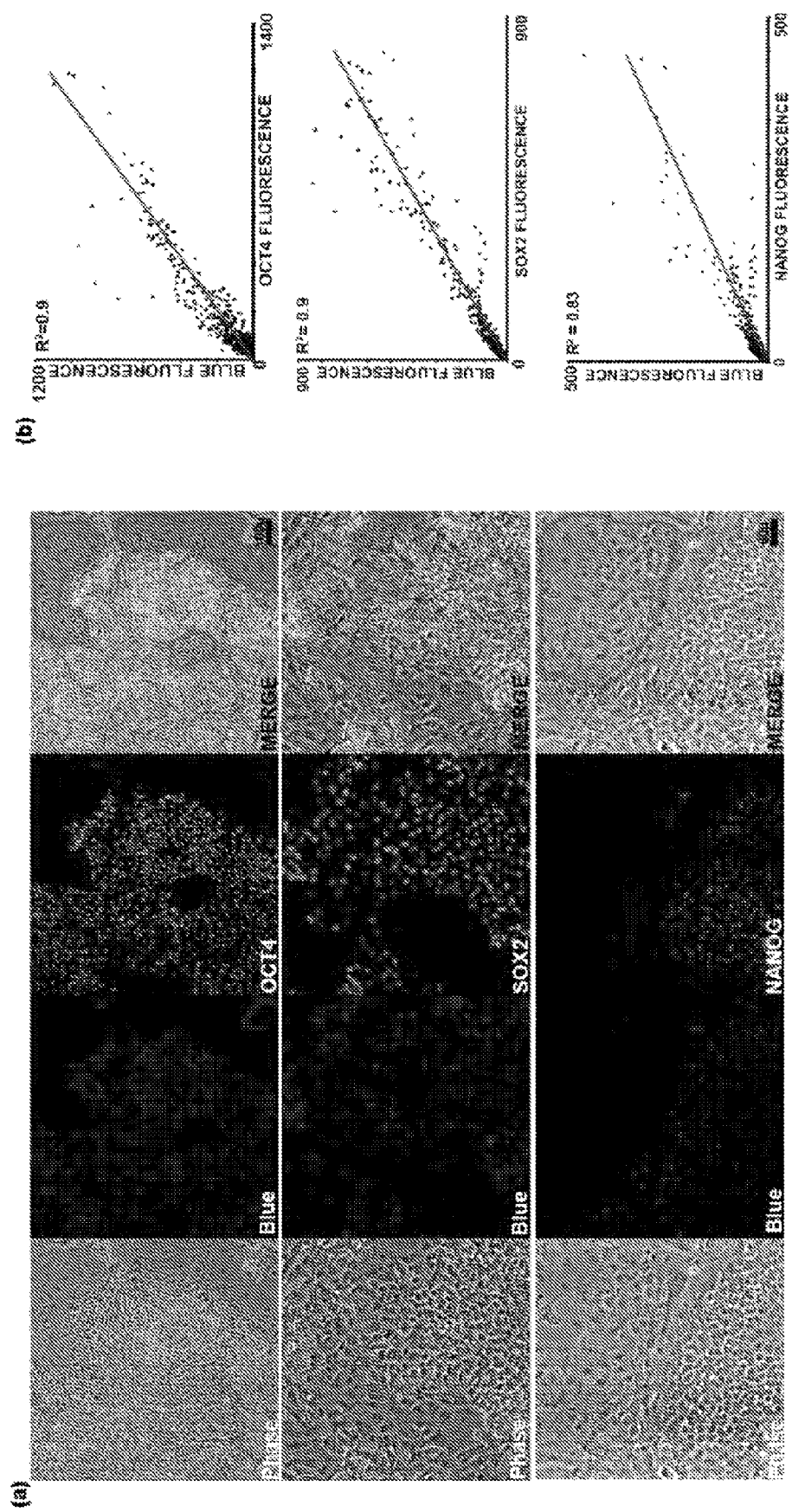
Figure 3:
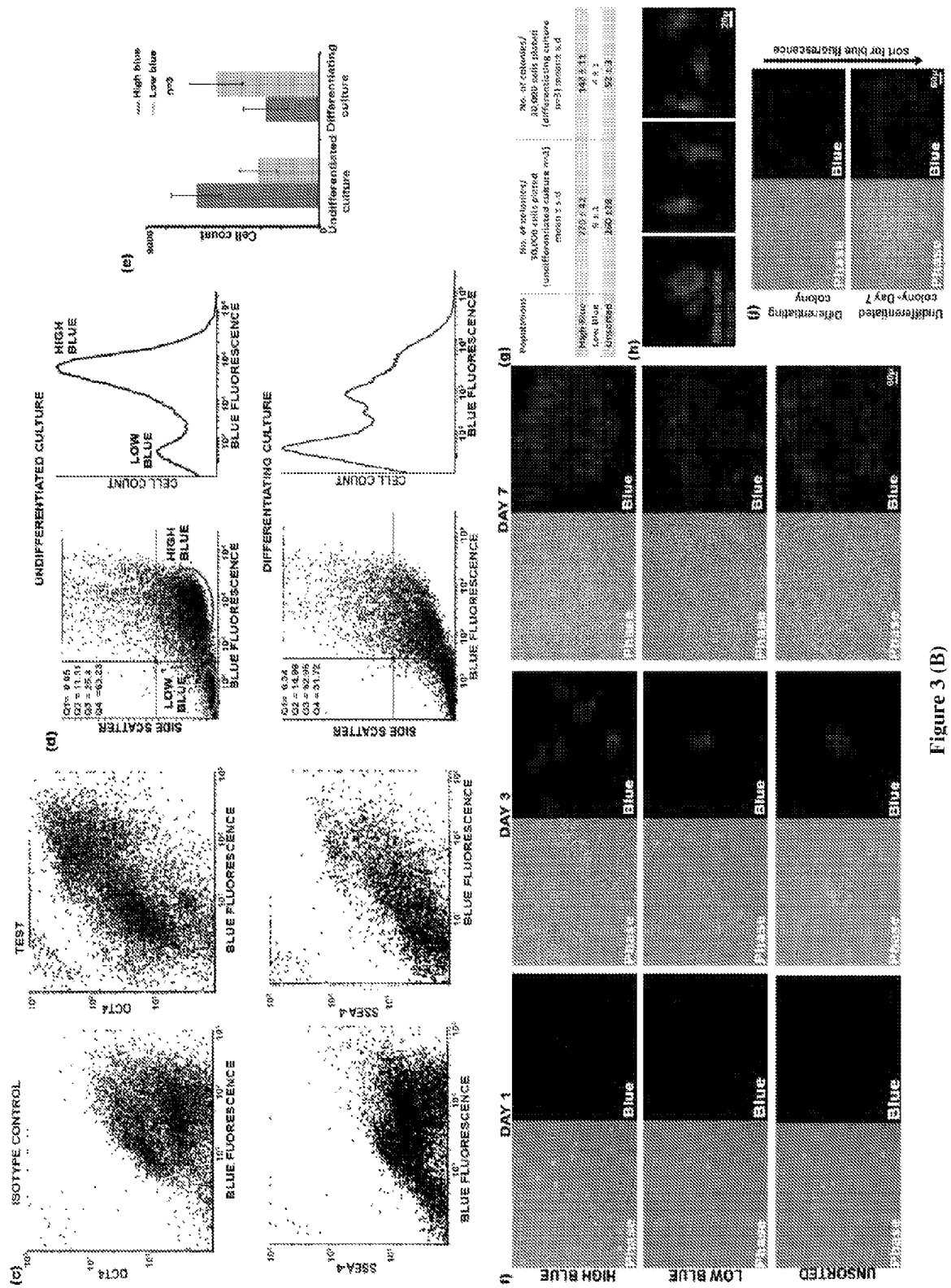

FIG. 3 shows that lipid body-associated blue fluorescence is a pluripotency marker and aids in easy isolation and high throughput single cell propagation of HPSCs.

(a) Lipid body associated blue fluorescence is co-expressed with pluripotency markers (OCT4, SOX2 and NANOG) in undifferentiated HuES7 cells. Differentiating regions identified by morphology (marked with red dashed line) shows absence of lipid body-associated blue fluorescence and pluripotency markers. (b) Scatter plots of mean fluorescence intensities of blue fluorescence vs pluripotency marker fluorescence (measured by marking equisized ROIs) shows positive correlation. (c) FACS analysis shows co-expression of blue fluorescence with OCT4 and SSEA-4 markers. (d) Typical FACS scatter plots and histograms of undifferentiated HPSCs show a larger high blue population while differentiating cultures show the reverse. (e) Cell counts from high blue and low blue cell populations of undifferentiated and differentiating cultures. (f) Typical colonies from sorted high blue, low blue and unsorted cells. (g) Colony counts from high blue, low blue and unsorted cells from undifferentiated and differentiating cultures. (h) 'Low blue' cells are viable, have active mitochondria and do not have characteristic HuESC morphology. (i) Isolation and propagation of HuESCs from highly differentiated HuES cultures obtained by plating cells from 'high' blue population. Q1=upper left quadrant, Q2=upper right quadrant, Q3=lower left quadrant, Q4=lower right quadrant.

Figure 4:
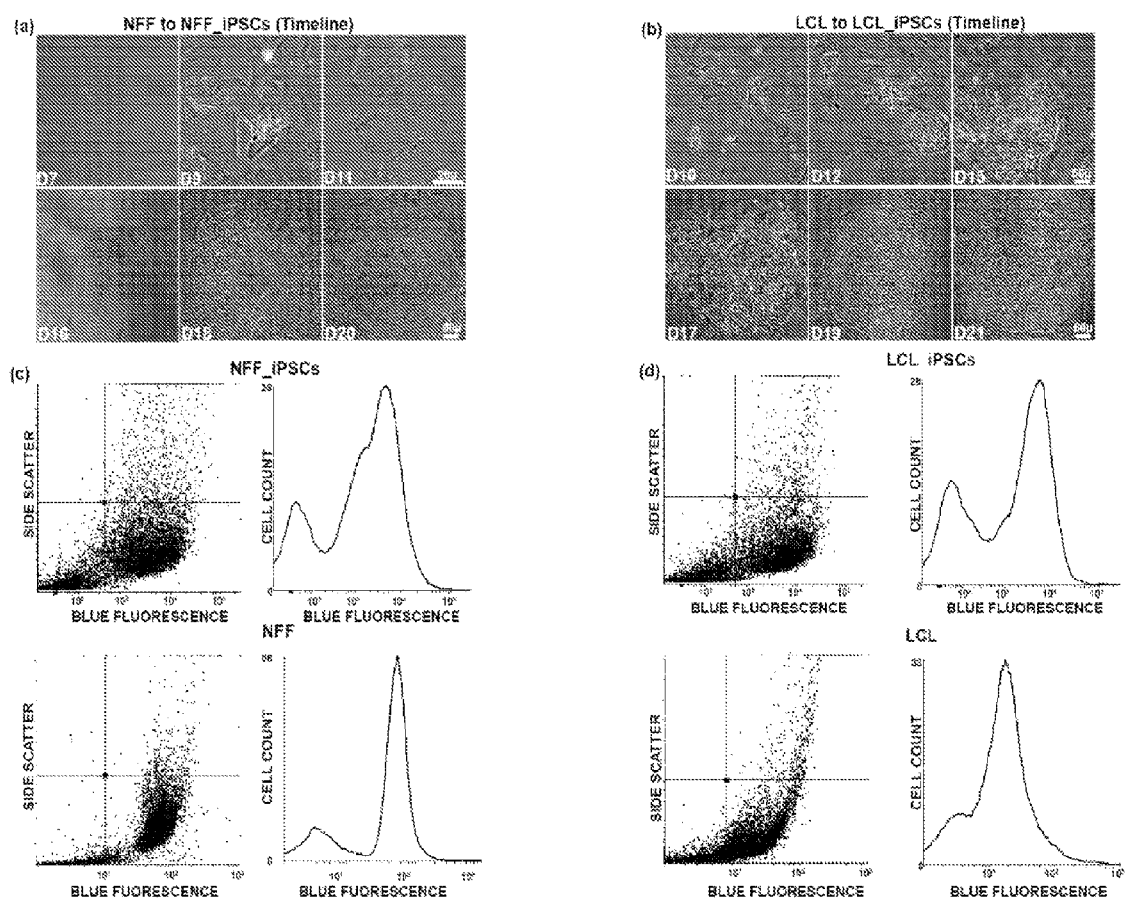

FIG. 4 shows that human somatic cells acquire fluorescent lipid bodies very early in reprogramming.

(a,b) Neonatal fibroblasts (NFF) and lymphoblastoid cells (LCL) show very early appearance of blue fluorescent lipid bodies (D(n)—days post transfection and plating). The background MEF feeder layer remains non-fluorescent. (c,d) The blue fluorescence FACS profiles of human induced pluripotent stem cells (HiPSCs (NFF iPSCs and LCL iPSCs) are similar and match closely with those of human embryonic stem cells (HuES7 (see FIG. 2c) and differ substantially from those of their somatic precursor. Please note—the horizontal scales in the lower scatter and profile plots are smaller.

Figure 5:
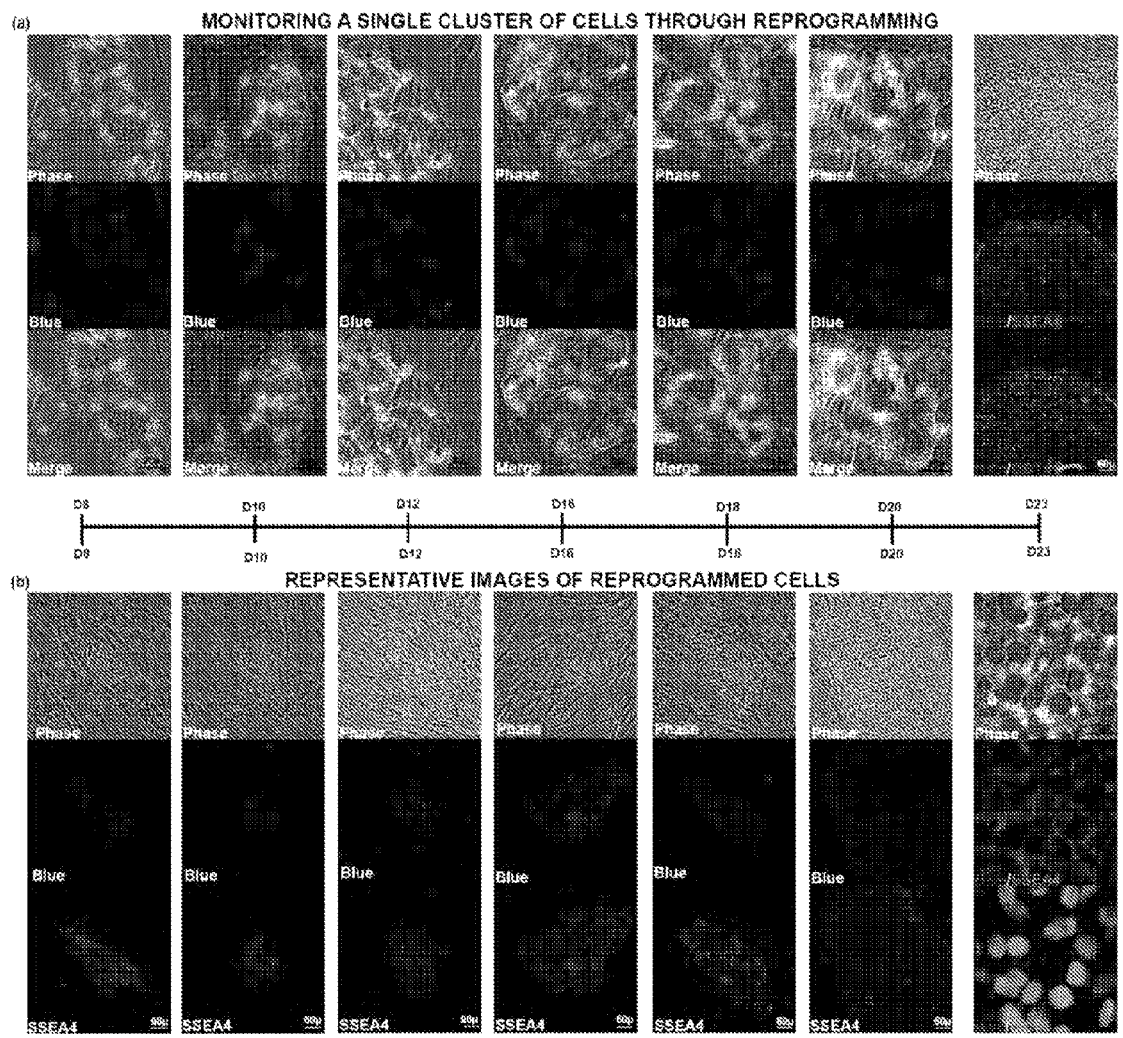

FIG. 5 shows a timeline of reprogramming and appearance of blue fluorescence in human somatic cells.

(a) A typical cluster of cells that showed flattened morphology and blue fluorescence post electroporation was followed from Day 8 (D8) to Day 23 (D23) and the resultant colony was stained for pluripotency markers (SSEAS4 and OCT4). (b) Cell clusters with blue fluorescent lipid bodies at D8 also show expression of SSEA4. Rightmost panel shows co-expression of blue fluorescent lipid bodies, OCT4 and SSEA4 in a reprogramming HiPSC.

Figure 6:
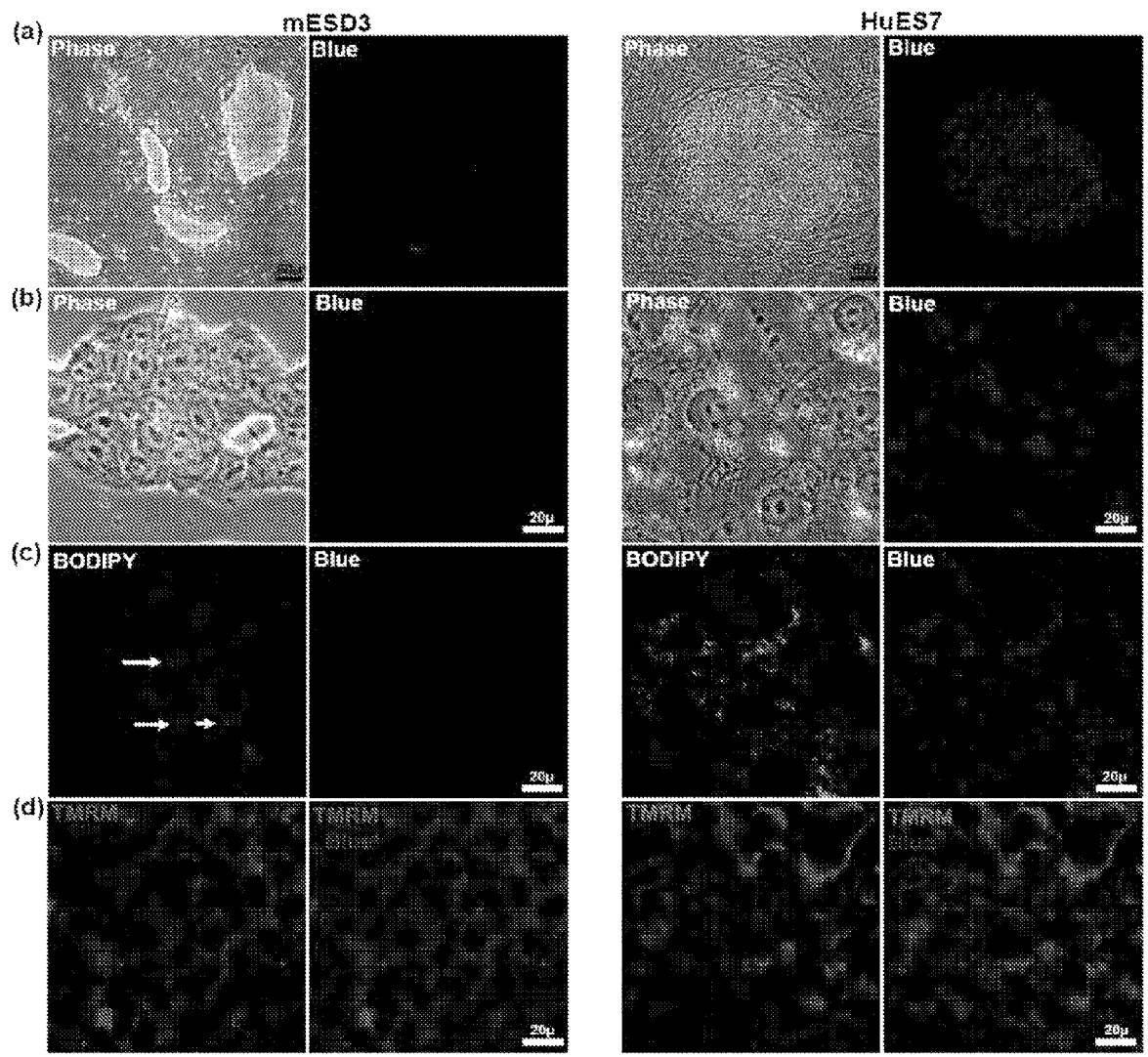
Figure 6:
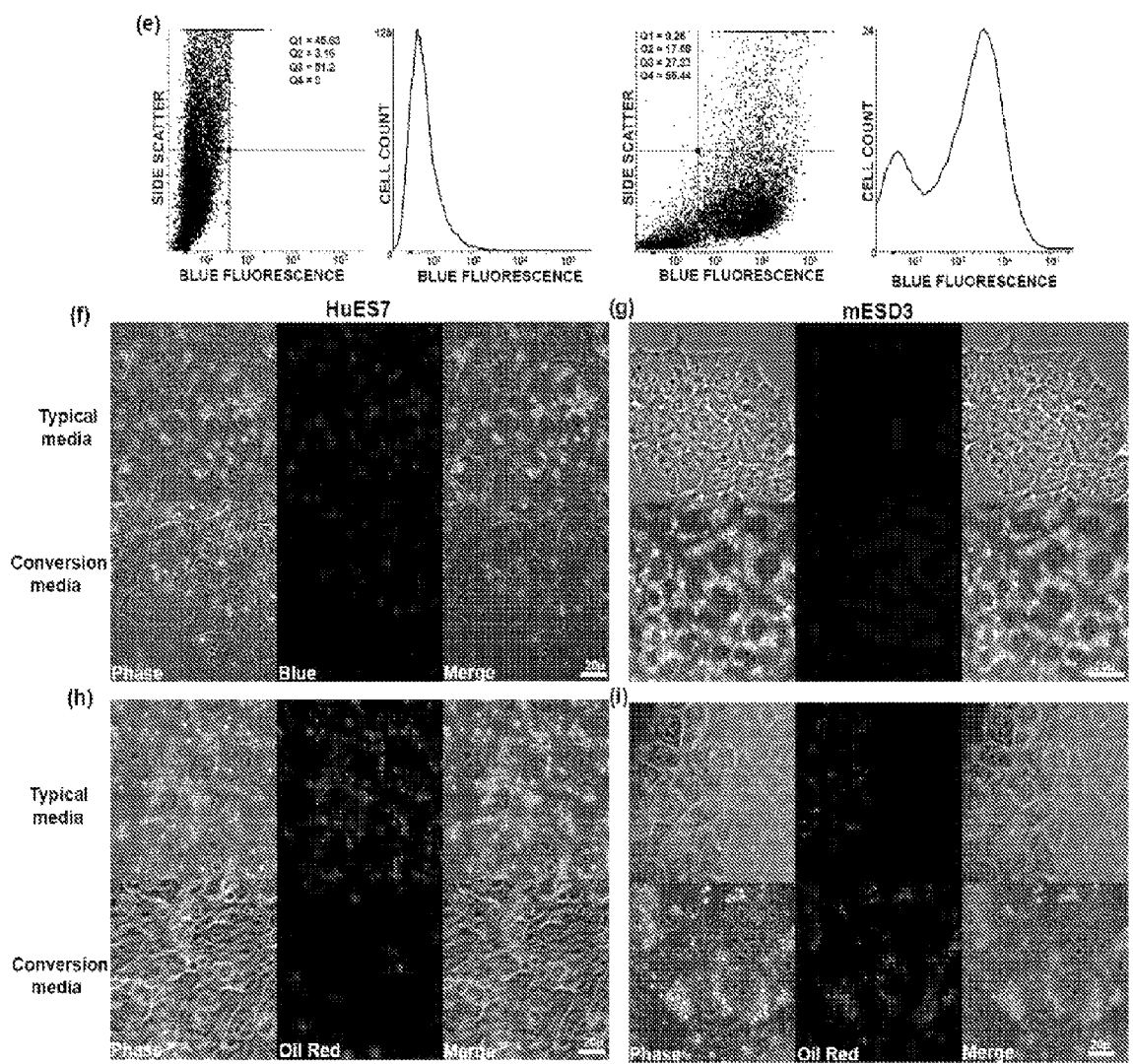

FIG. 6 shows that blue fluorescent lipid bodies mark 'primed' or 'epiblast' state pluripotent stem cells.

(a,b) Representative phase contrast and fluorescence images (low and high magnification) of Mouse ES-(mES-D3) and human ES (HuES7). mES-D3 cells have far lower blue fluorescence compared to HuES7. (c) BODIPY®493/503 stain and blue fluorescence high magnification images of mES-D3 and HuES7. Mouse ES cells show occasional lipid bodies (white arrows) which are not fluorescent unlike HuES cells. (d) The faint blue fluorescence observed in mES cells co-localizes with the mitochondria-specific dye—TMRM (R2=0.93). (e) Typical FACS profiles of mouse and human ES cells show the mES cell to have lower unimodal fluorescence levels while the HuES cells have a bimodal distribution. (f,h—upper panel) HuES7 cells grown in typical HuES media have blue fluorescent lipid bodies. (g,i—upper panel) Mouse ES cells grown in typical mES media have very few lipid bodies. The faint blue fluorescence observed in mES cells emanates from mitochondria (see FIG. 4d) (f,h—lower panel) HuES7 cells grown in media that promotes conversion to the 'naive' state show a substantial decrease in the number of lipid bodies (Oil Red-positive) with a corresponding decrease in blue fluorescence. (g,i—lower panel) Mouse ES-D3 cells grown in media that promotes conversion to the 'primed' or 'epiblast-like' state show a substantial increase in the number of lipid bodies (Oil Red-positive), which have blue fluorescence. Q1=upper left quadrant, Q2=upper right quadrant, Q3=lower left quadrant, Q4=lower right quadrant.

Figure 7:
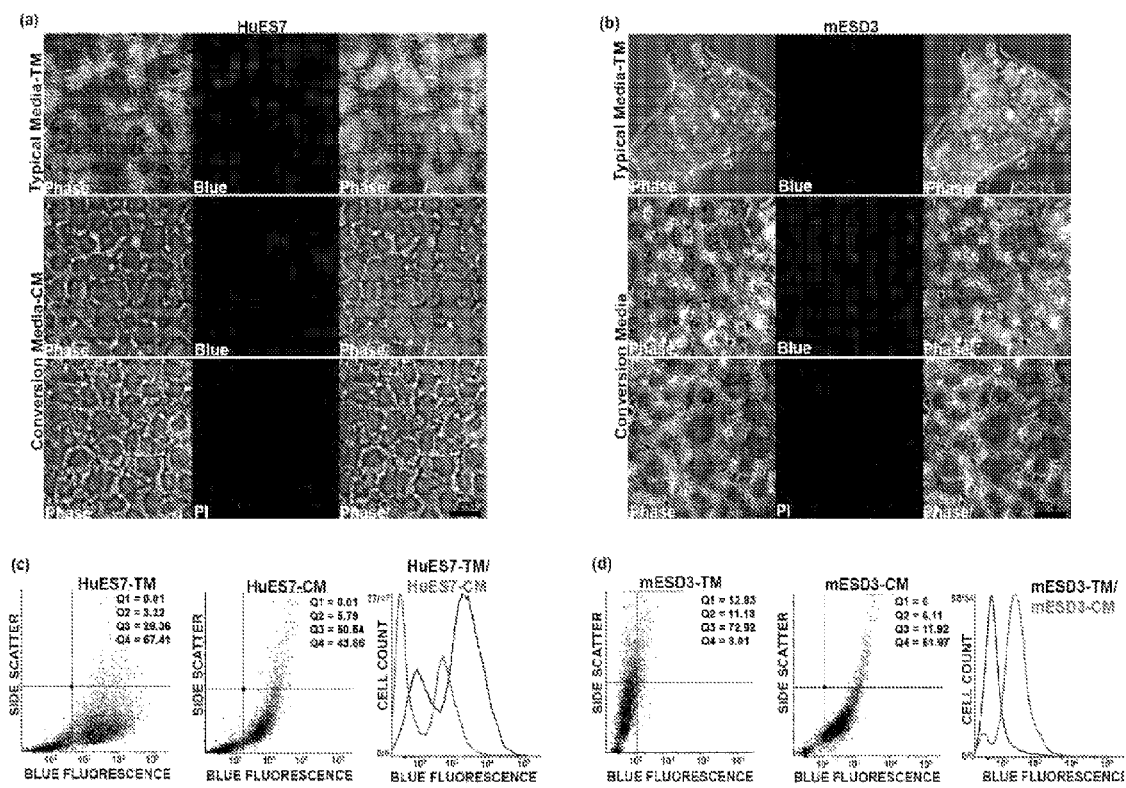

FIG. 7 shows in vitro characterization of human (primed) to 'naive' and mouse (naive) to 'primed' pluripotent stem cells.

(a,b) Representative images (high magnification) of HuES7 ('primed') and mESD3 ('naive') cultured in typical media (TM) and conversion media (CM) show difference in the morphology (phase image) and number of blue fluorescent lipid bodies and intensity of OCT4 fluorescence (top and middle panel). These cells remain viable and pluripotent in the conversion media, express OCT4 and are negative for Propidium iodide (PI) staining (c,d) FACS profile of HuES7 in conversion media show the number of high blue cells to have decreased and the number of low blue cells to have increased. The opposite effect is observed is mES cells cultured in conversion media. Q1=upper left quadrant, Q2=upper right quadrant, Q3=lower left quadrant, Q4=lower right quadrant.

Figure 8:
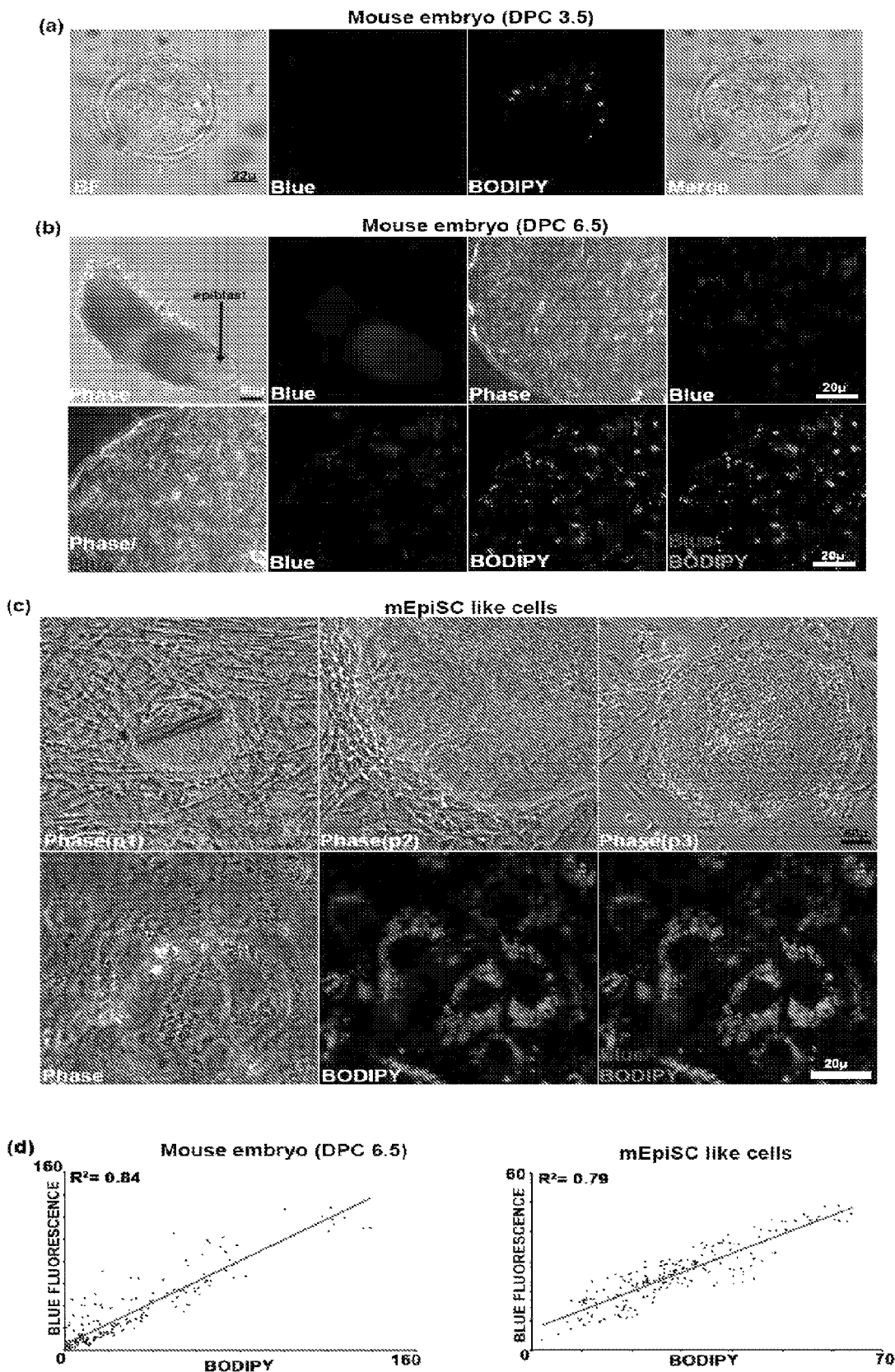

FIG. 8 shows that blue fluorescent lipid bodies are absent in the mouse blastocyst inner cell mass (ICM), and present in many mouse epiblast cells and also in mEpiSC like cells.

Figure 9:
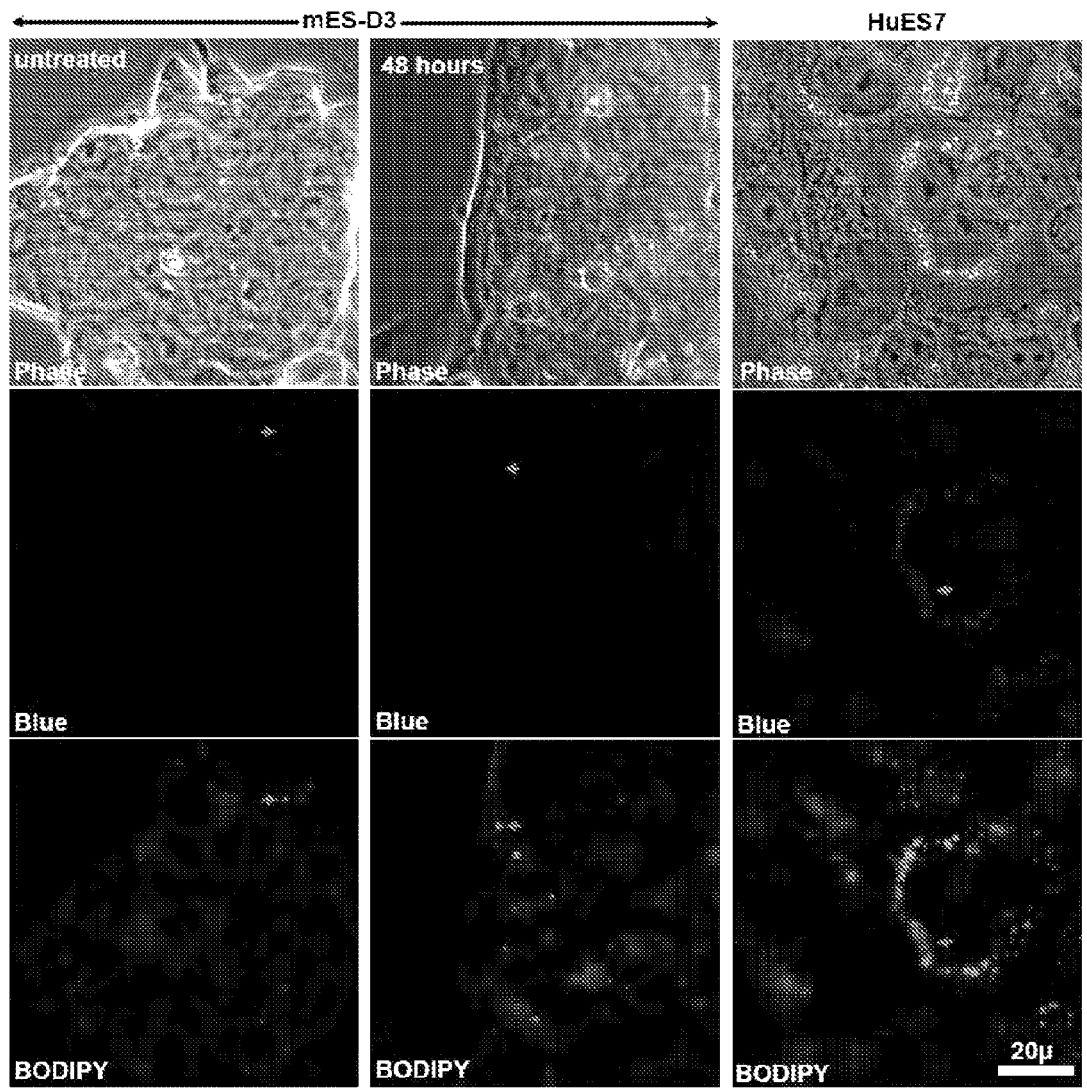

(a) Fluorescent lipid bodies are absent in the inner cell mass (ICM) of the DPC 3.5 mouse embryo. (b—upper panel) DPC 6.5 mouse embryo show high levels of blue fluorescence differentially distributed. High magnification of the epiblast region shows numerous blue fluorescent puncta. (b—lower panel) Blue fluorescence puncta in the epiblast region are stained by BODIPY®493/503. (c) Mouse epiblast stem cells (mEpiSC) cultured from mouse embryo (DPC 6.5) in mEPiSC media (K15F5) and sequentially passaged (p1, p2 and p3) retain blue fluorescent BODIPY®493/503 positive lipid bodies. Lower panel shows cells from a p3 culture at high magnification and co-localization of blue fluorescence with BODIPY®493/503. (d) Scatter plots of BODIPY®493/503 mean fluorescence intensities vs mean blue fluorescence intensities in the post-implantation mouse embryo (DPC 6.5) and in mEpiSC-like cells show high positive correlation. BF—Bright field FIG. 9 shows that mouse ES cells do not take up retinol from the media and sequester them in lipid bodies.

Mouse ES cells grown in 20% KOSR with or without additional retinol do not show any increase in blue fluorescence and do not show any significant increase in the number of lipid bodies unlike HuES7 cells (see FIG. 10e,g).

Figure 10:
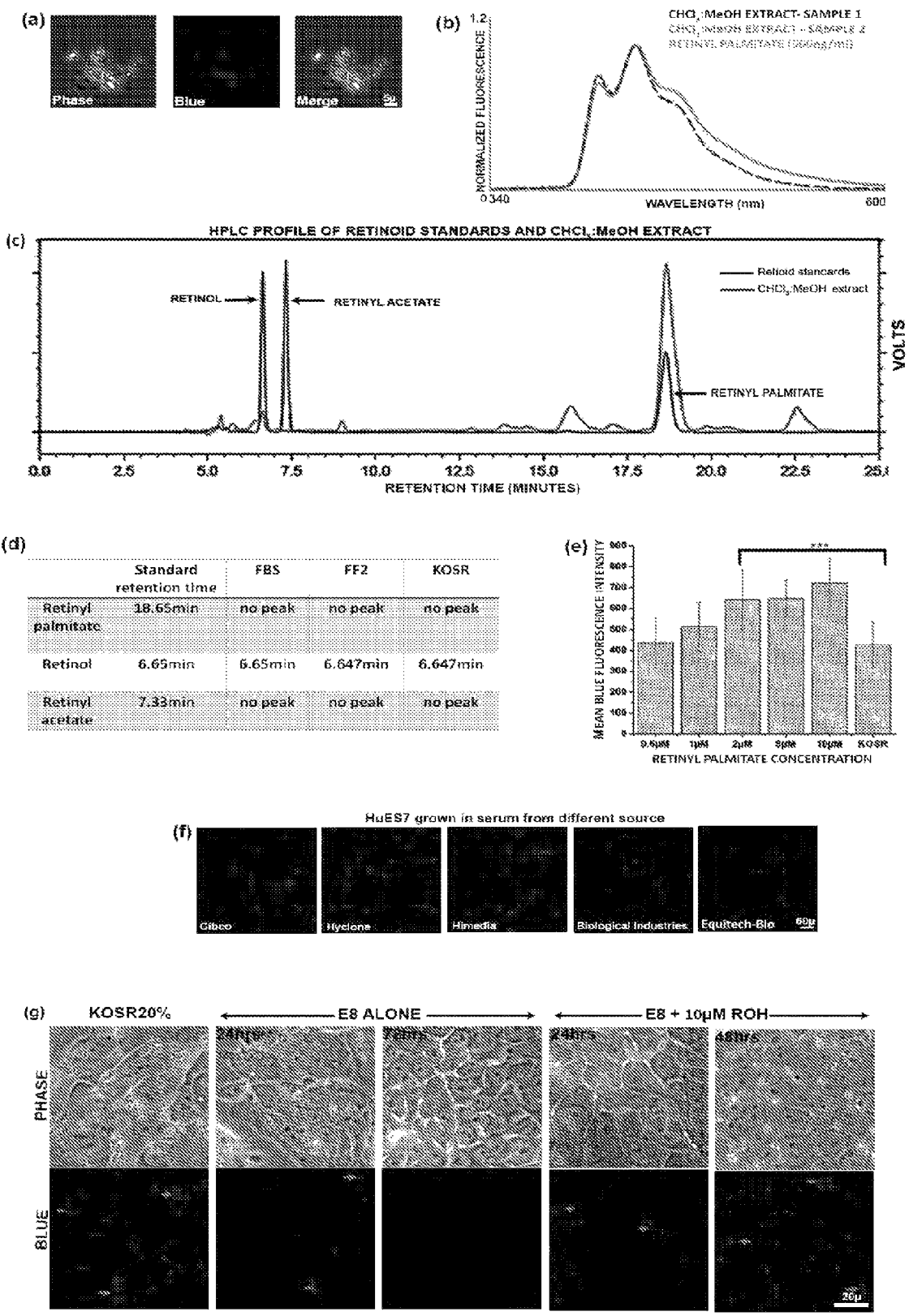

FIG. 10 shows that the blue fluorescence in lipid bodies arises from retinoids obtained from sera or serum replacement components.

(a) Lipid bodies isolated from HuES7 cells using sucrose gradient centrifugation retain blue fluorescence. (b) Chloroform:methanol extracts of fluorescent lipid bodies and retinyl palmitate have identical fluorescence spectra. The fluorescence traces of individual samples were normalized to their maximum emission values. (c) C18 Reverse HPLC of the chloroform:methanol extract and retinyl standards show the main peak of the extract and retinyl palmitate to have identical retention times. (d) Reverse phase HPLC analysis of chloroform:methanol extracts of FBS and serum-free commercially available ES grade media show presence of retinol. (e) Lipid bodies in cells cultured in typical HuES cell media supplemented with retinyl palmitate show dose dependent increase in blue fluorescence. (f) HuES7 cells cultured in typical human ES media with serum from 5 different sources replacing KOSR have blue fluorescent lipid bodies. (g) HPSCs cultured in chemically defined E8 media (lacks retinol) show a steep decrease in lipid bodies (red arrows) and blue fluorescence with time, and regain blue fluorescent lipid bodies in 48 hours when E8 is supplemented with retinol. Significance level *** is <0.001

DETAILED DESCRIPTION OF THE DISCLOSURE

The present disclosure relates to a method for identifying pluripotent stem cell in a culture and optionally isolating the pluripotent stem cell from the culture, said method comprising acts of:
  a) subjecting the culture to excitation at wavelength ranging from about 275 nm to about 410 nm for obtaining endogenous blue fluorescence emission from lipid body present within the pluripotent stem cell; and b) measuring intensity of the emission for identifying the pluripotent stem cell in the culture;

c) optionally sorting the culture for isolating the pluripotent stem cell from the culture.

In an embodiment of the present disclosure, the culture comprises cells selected from a group comprising non-differentiating stem cell(s), differentiating stem cell(s), differentiated stem cell(s), cell(s) having or suspected of having pluripotent stem cell(s) and combination thereof.

In another embodiment of the present disclosure, the excitation is from single photon source or multiphoton source.

In yet another embodiment of the present disclosure, the intensity of endogenous blue fluorescence emission is at wavelength ranging from about 410 nm to about 550 nm.

In still another embodiment of the present disclosure, the endogenous blue fluorescence emission is detected using technique selected from a group comprising fluorescence microscopy, epifluorescence microscopy, dual microscopy, multiphoton microscopy and combination thereof.

In still another embodiment of the present disclosure, the pluripotent stem cell is selected from a group comprising human embryonic stem cell (HuESC), human induced pluripotent stem cell (HiPSCs), mouse epiblast pluripotent stem cell (mEpiSC), mammalian stem cell and combination thereof.

In still another embodiment of the present disclosure, the human induced pluripotent stem cell (HiPSCs) is selected from a group comprising human lymphoblastoid induced pluripotent stem cell (LCL iPSCs), human neonatal foreskin fibroblast induced pluripotent stem cell (NFF iPSCs), adult dermal fibroblast induced pluripotent stem cell (ADF iPSCs) and combination thereof.

In still another embodiment of the present disclosure, the sorting is carried out by Fluorescence Activated Cell Sorting technique.

In still another embodiment of the present disclosure the blue fluorescence arises from retinoids within the lipid bodies of pluripotent stem cells.

In still another embodiment of the present disclosure, said method is employed for high throughput propagation of human pluripotent stem cell.

In still another embodiment of the present disclosure, the pluripotent stem cells are naïve or primed or both.

In still another embodiment of the present disclosure, the primed pluripotent stem cells are epiblast-like pluripotent cells.

The present disclosure relates to a method to identify and isolate human pluripotent stem cells using endogenous fluorescence emanating from lipid bodies present within the pluripotent stem cells. The property of fluorescence is an inherent property of only such lipid bodies which are present in the pluripotent stem cells; and not all the lipid bodies have the property of auto-fluorescence. Hence, the lipid bodies of the instant disclosure are stage and cell specific in nature.

In an embodiment of the present disclosure, it is observed that human embryonic stem cells (HuESC) and human induced pluripotent stem cells (HiPSC) contain spherical lipid bodies which emit endogenous blue fluorescence, and serve as label free endogenous marker for the pluripotent state [FIGS. 1, 2, 3]. FIG. 1 shows that human pluripotent stem cells have cytoplasmic lipid bodies that have a characteristic blue fluorescence. Phase images are shown above and their corresponding fluorescence images are shown below in the said figure. In these figures, LCL is lymphoblastoid cell line, NFF is neonatal foreskin fibroblasts, ADF is adult dermal fibroblasts and MEF is mouse embryonic fibroblasts, which are all somatic cells that lack endogenous blue fluorescence.

In another embodiment of the present disclosure, when human embryonic stem cells and human induced pluripotent stem cells differentiate spontaneously or are made to differentiate, the lipid bodies with endogenous blue fluorescence are not observed when subjected to excitation using either a single photon excitation source at wavelength ranging from about 275 nm to about 410 nm, preferably around 325 nm to 375 nm, near or at UV region [FIG. 3], or a multiphoton source at appropriate wavelength, enough to excite the endogenous fluorophore present within the pluripotent stem cell.

The present disclosure allows one to monitor, identify and isolate human pluripotent stem cells (embryonic and induced) and mouse epiblast-like pluripotent stem cells using endogenous blue fluorescence from intracellular lipid bodies which emanate from "retinoid" or "retinoid-like" compounds present in these lipid bodies.

In an embodiment of the present disclosure, the blue fluorescence arises from sequestration of retinoids, primarily retinyl esters within the lipid bodies of human pluripotent stem cells.

In another embodiment of the present disclosure, supplementing culture media with retinol or retinyl palmitate causes a dose-dependent increase in the blue fluorescence within lipid bodies of human embryonic stem cells indicating retinoid uptake from the culture media and its sequestration within lipid bodies.

In yet another embodiment of the present disclosure, the lipid bodies that sequester retinoids mark the 'epiblast-like' state in vivo and in vitro and serve as a useful marker to distinguish between 'naïve' and 'primed' pluripotent stem cells.

In still another embodiment, the method described in the instant disclosure is label-free, i.e. uses only the endogenous blue fluorescence intensities associated with the lipid bodies and does not use the ratio of NADH fluorescence intensities with the LDAG fluorescence intensities as an indicator of differentiated or undifferentiated pluripotent stem cells.

In accordance with the method of the instant disclosure, the identification of pluripotent stem cells is done when the endogenous fluorophore of the pluripotent stem cells is subjected to excitation with the appropriate light source/wavelength, and emits endogenous blue fluorescence. The excitation of the pluripotent stem cells is done using either a single photon excitation source at wavelength ranging from about 275 nm to about 410 nm, preferably around 350 nm or a multiphoton source at appropriate wavelength, enough to excite the endogenous fluorophore present within the pluripotent stem cell.

In another embodiment, in the instant disclosure, the UV laser with appropriate filters are used in FACS and a metal halide lamp or a light source, including lasers, that generates UV light along with appropriate filters are used in the epifluorescence microscope. The excitation on the pluripotent stem cells is around 325 nm to 375 nm and emission is observed around 410 nm to 500 nm as a blue fluorescence of 410 nm to 500 nm from the lipid bodies present within them. For Microscope and example of filters used would be—Excitation is at 325 nm-375 nm; 426 nm-446 nm, the Dichroic used—460dc xru; and the Emission is around 460 nm-500 nm. For FACS in an example the excitation is around 375 nm, near UV, Trigon detector for blue fluorescence and collected at around 450/50 nm bandpass filter. The instant technique does not involve staining and is a label free method.

In yet another embodiment of the present disclosure, the endogenous blue fluorescence is monitored using a standard fluorescence microscope with appropriate filters, which allows for both identification and mechanical isolation of human pluripotent cells. In an example, the microscope used is a Nikon Eclipse TE 2000. The filters used for observing the endogenous blue fluorescence in an example were from Chroma (Excitation—325-375; 426-446 nm, Dichroic—460dc xru, Emission—460-500 nm). The objectives used ranged from about 10× to about 60× [FIGS. 1 to 10].

In still another embodiment of the present disclosure, two overlapping but distinct distributions of endogenous blue fluorescence are seen when cultures of primarily human pluripotent cells are sorted in a FACS machine as detailed (BD FACS Aria cell sorter, laser—375 nm near UV, Trigon detector for blue fluorescence and collected at 450/50 nm bandpass filter (DAPI channel); PMT voltage set at 350V for blue fluorescence). The distribution with higher endogenous blue fluorescence contains more pluripotent cells i.e. cells that fall within the higher blue fluorescence profile also give rise to more number of pluripotent stem cell colonies on plating [FIGS. 3 and 6].

In still another embodiment of the present disclosure, cells with higher blue endogenous fluorescence are separated easily and reliably from the non-pluripotent population as single cells using the endogenous blue fluorescence (FIG. 3).

The present technique is used with a standard fluorescence microscope and filters; and can also use standard fluorescence-activated cell sorters which are able to visualize fluorescence with a 450/50 nm bandpass filter (for e.g. the DAPI channel) to identify, quantify and isolate pluripotent human stem cells, both embryonic and induced. With FACS, it is used to sort out the pluripotent cells and with fluorescence microscopes one can mechanically dissect out areas containing pluripotent stem cells from differentiated cells by monitoring the endogenous blue fluorescence. The instant disclosure describes a method which easily lends itself to high throughput identification, isolation and propagation of human pluripotent stem cells unlike the FLIM method.

In an embodiment, repeated sorting and propagation of human pluripotent stem cells does not alter their blue fluorescence distribution profiles indicating that the sorted cells continue to behave like regular HPSCs and those with high blue fluorescence retain pluripotency.

In another embodiment, somatic cells do not have spherical lipid bodies that emit this endogenous fluorescence, but do when converted to the pluripotent state. It was initially shown by Yamanaka and co-workers that transcription factors like Oct4, Sox2, Nanog, Klf, C-Myc, N-Myc, Lin28 can convert somatic cells, when expressed in the right combinations and levels to generate induced pluripotent stem cell colonies. These factors are expressed by transfecting or infecting somatic cells with plasmids, viruses or RNA transcripts that encode these proteins. Proteins can also be directly transferred into cells using cell-penetrating peptides. Small chemical molecules have also been identified that allow for the endogenous expression of these proteins. On sustained expression of these exogenous transcription factors and in the appropriate media which would include the appropriate growth factors, the somatic cells begun to convert to pluripotent stem cells. The endogenous genes that encode OCT-4, Klf4, Nanog, SOX-2 in the somatic cells also begin to express and the cells become pluripotent stem cells. The continued presence of the exogenous transcription factors is no longer essential. Under most of these conditions only a small percentage of cells undergo conversion to pluripotency. As the somatic cells undergo reprogramming, lipid bodies with endogenous blue fluorescence appear even before typical iPSC colonies are formed [FIGS. 4 and 5]. FIG. 4 shows that human somatic cells acquire fluorescent lipid bodies very early in reprogramming. The FIG. 4 captures merged phase contrast and blue fluorescence images of an NFF and LCL transfected the episomal plasmids encoding human OCT4, SOX2, L-Myc, Klf4, Lin-28 and p53-shRNA (Addgene plasmid nos: 27076, 27078, 27080) obtained from the Yamanaka Laboratory through Addgene, USA and used according to the method by Okita et al. 2011. which are followed through multiple days up-to the formation of iPS colonies. The Yamanaka's factors are protein transcription factors, such as Oct-4, Sox-2, Klf4, L-Myc, that when expressed together in somatic cells, convert them into pluripotent stem cells, i.e., iPSC colonies. In the figure, D is days in culture post-transfection.

In another embodiment, the endogenous blue fluorescence along with the lipid bodies are characteristic of the epiblast state of human pluripotent stem cells. Mouse ES cells which are considered to be in the 'naïve' state do not have any lipid bodies with endogenous blue fluorescence. Low levels of blue endogenous fluorescence are observed in mouse ES cells which emanates from their mitochondria [FIG. 6].

In yet another embodiment, human pluripotent cells, when grown in culture conditions that are known to make them more mouse ES-like i.e. the more 'naive' state, show a decrease in number of lipid bodies with endogenous blue fluorescence and mouse ES cells when grown under conditions that would favor the epiblast state (mEpiSC) show an increased number of larger lipid bodies and these bodies acquire blue fluorescence [FIG. 6].

The present disclosure allows one to monitor, identify and isolate human pluripotent stem cells (embryonic and induced) using an endogenous blue fluorescence from intracellular lipid bodies. The blue endogenous fluorescence is also used to follow reprogramming and also to distinguish pluripotent stem cells and differentiated cells from each other. Furthermore, the lipid bodies also help to identify stem cells in the 'primed' or epiblast state from the more primitive state or 'naive' state [FIGS. 1 to 10].

In another embodiment of the instant disclosure, endogenous blue fluorescence is retained within the lipid bodies even in cells fixed with paraformaldehyde [FIGS. 2 and 3].

In yet another embodiment of the instant disclosure, the experimental results are confirmed by way of conducting various tests such as presence of specific pluripotent markers e.g. Oct-4, Sox2 and Nanog and its association with Oil red staining and subsequent expansion of the sorted cell population. The Oil red staining is carried out to confirm that the spherical bodies that emit endogenous blue fluorescence are indeed lipid bodies.

In an embodiment of the present disclosure, pluripotent cells depict the presence of various pluripotent markers such as Oct-4, Sox2, Klf4, C-Myc, Lin28, SSEA-4, SSEA-3, Alkaline phosphatase, Tra-1-60, Tra-1-81-etc. Levels of Oct-4 protein, Sox2 and Nanog pluripotency (stem cell) markers are determined by immunofluorescence, which show positive correlation with levels of endogenous blue fluorescence. In spontaneously differentiating human pluripotent stem cell colonies i.e. the areas, which by morphology look differentiated do not exhibit endogenous blue fluorescence and cells in these areas also do not express or have very low levels of Oct-4 in their nuclei [FIG. 3]. Cultures of differentiating human pluripotent stem cells when sorted, show increased numbers of cells with lower endogenous blue fluorescence [FIG. 3].

The present disclosure relates to identifying and isolating human induced pluripotent stem cells from their differentiating counterparts; and mouse and human pluripotent stem cells in embryonic and epiblast states. The technique is label-free, is suited for high throughput identification, easy mechanical dissection, isolation, and subsequent propagation. The method employs standard fluorescence microscope and FACS machine and does not involve any expensive equipment. The present disclosure does not employ FLIM and phasor plots to identify and separate fluorescence from NADH and LDAG. Further, the current invention does not mention that the presence of fluorescence in lipid bodies in pluripotent stem cells is due to reactive oxygen species.

The method described in the instant disclosure, is robust, is easily and directly applied with standard equipment available in most laboratories and does not require specific expertise or training or very sophisticated instruments.

The method described in the instant disclosure is used to demonstrate that the endogenous blue fluorescence is perceptible very early in the process of conversion of human somatic cells to iPS cells and therefore serves as an early marker of reprogramming and helps monitor the process of conversion to pluripotency. In the prior art, the efficiency of reprogramming could be estimated only by visualizing the appearance of colonies by morphology and appearance of markers like Oct-4-GFP using genetically modified starting cells, hence the instant disclosure overcomes the said drawback.

Reciprocally, it is used to follow the process of differentiation and remove teratoma-forming pluripotent stem cells, for e.g. prior to in vivo transplantation of the differentiated cells. Pluripotent stem cells can form teratomas on transplantation. Teratomas, which are tumors, are usually benign, but have the potential to generate malignant tumors and also other types of differentiated cells of all three germ layers. These cells would also interfere with the functioning of the transplanted cells. In the prior art, the removal of pluripotent cells from the differentiated population required the use of antibodies or genetically modifying the cells and hence this disclosure overcomes the said drawback.

In an embodiment, the Mouse ES cell lines (ES D3 and ES R1) are both obtained from American Type Culture Collection (ATCC), wherein ES D3 is derived from strain 12952/SvPas mouse blastocyst and has the ATCC No: CRL-1934.

The source of ES R1 is from Dr. Andras Nagy, Lunenfeld-Tanenbaum Research InstituteMount Sinai Hospital Joseph & Wolf Lebovic Health Complex600 University Avenue Toronto Ontario. ES R1 is established from 3.5 day blastocysts produced by crossing two 129 mouse substrains (129S1/SvlmJ and 129X1/Svj) and has the ATCC no. SCRC-1011. The human embryonic stem cell HuES7 is obtained from Dr. Doug Melton, Harvard University, USA. This line was generated through Boston IVF collaboration with Harvard University and Howard Hughes Medical Centre and is available from Dr. Doug Melton. The source of these cells and details are available in "Derivation of embryonic stem-cell lines from human blastocysts." Authors—Cowan C A, Klimanskaya I, McMahon J, Atienza J, Witmyer J, Zucker J P, Wang S, Morton C C, McMahon A P, Powers D, Melton D A. Journal—N. Engl. J. Med. 2004 Mar. 25; 350(13):1353-6. Epub 2004 Mar. 3.

Source of LCL, ADF and NFF: Geriatric Clinic, National Institute of Mental Health and Neurosciences (NIMHANS).

In an embodiment of the present disclosure, the technology of the instant Application is further elaborated with the help of following examples and figures. However, the examples should not be construed to limit the scope of the disclosure.

EXAMPLES

Materials and Instrumentation—
Human and Mouse Pluripotent Stem Cell Culture
The human embryonic stem cell line (HuES7) and human induced pluripotent stem cells lines (LCL iPSCs, NFFs iPSCs and ADF iPSCs) are maintained as undifferentiated colonies on mitotically-inactivated mouse embryonic fibroblasts (MEFs) feeder layers in typical HuES culture medium (KO-DMEM (Invitrogen, USA), about 100 µM 2-Mercaptoethanol (Sigma-Aldrich, USA), about 20% knockout serum replacement (KOSR—Invitrogen, USA), about 10 nM non-essential amino acids, about 100 mM L-glutamine and about 5 ng/ml recombinant human basic fibroblast growth factor (bFGF) (Peprotech, Israel) at about 5% $CO_2$ and about 37° C. Mouse embryonic stem cells (mES) R1 and D3 are cultured in typical mES culture medium on mitotically-inactivated MEFs (KO-DMEM, about 15% KOSR, about 10 nM non-essential amino acid, about 200 mM L-glutamine and $10^6$ units/ml of Leukaemia Inhibiting Factor (LIF) (Chemicon, USA) at about 5% $CO_2$ and about 37° C. Media changes are on alternate days unless stated otherwise. Colonies are passaged either by enzymatic dissociation with Accutase (Invitrogen, USA) or mechanically dissociated and transferred onto fresh MEFs when 70-80% confluent. The human iPSCs lines are generated in the lab by electroporation (Neon, Invitrogen, USA) of somatic cells (LCLs or human adult (ADF) or neonatal foreskin (NFF) fibroblasts) with episomal plasmids encoding human OCT4, SOX2, 1-Myc, Klf4, Lin-28 and p53-shRNA obtained from Addgene, USA according to the method of Okita, K. et al. (A more efficient method to generate integration-free human iPS cells. Nature methods 8, 409-12 (2011)).

Microscopy and Image Analysis
All non-confocal epifluorescence images are obtained with a Nikon Eclipse TE2000-E-PFS (Japan) microscope with a Photometrix Cascade II 512 EM-CCD camera (Roper Scientific, USA) and Image Pro-Plus AMS software (Media Cybernetics, USA). The Nikon objectives used are 60×/NA1.4 oil immersions and 10×/NA 0.3 for all experiments. Fluorescence is visualized using band pass filters (Chroma Technology, USA). The filters used are Blue (Exciter—350 nm/50, Dichoric—400 nm long pass, Emitter—460 nm/50), Green (Exciter—500 nm/20, Dichoric—535 nm/30, Emitter—515 long pass) and Red (Exciter—450 nm/30, Dichoric—620 nm/0, Emitter—570 long pass). Confocal images are acquired using a Zeiss LSM 510 Meta Confocal set up with a 63× objective and a 405 laser (excitation—405 nm, emission—about 420 nm to about 490 nm). All images are processed using ImageJ 1.47 software. For qualitative depiction of images 16 bit grey scale images are imported into ImageJ, background subtracted and auto-adjusted. The processed files are saved as RGB images and final figures constructed using Adobe Photoshop CS3 using appropriate pseudo colours. For quantitative analysis and depiction of images for direct comparison, for e.g. between mouse ES cells and human ES cells, all the images presented have the same intensity scale bounded by the adjusted maximum value of the HuES cell image. Scatter plot and linear fit analyses of pluripotency marker expression (OCT4, SOX2 and Nanog) and blue fluorescence is performed with fluorescence intensity values of individual pixels using the 'plot profile' application from ImageJ.

Immunocytochemistry

Cells are cultured on MEFS on coverslip dishes. Cells are fixed in about 4% paraformaldehyde in HBSS with $Ca^{2+}$ and $Mg^{2+}$ (Invitrogen, USA), rinsed and permeabilized with about 0.1% Triton in PBS and incubated with blocking solution (about 0.3% BSA, 1×PBS and about 4% normal goat serum) at room temperature for one hour. The following primary antibodies are used: Anti-OCT4 antibody (cat no. C10 sc5279) from Santa Cruz Biotechnology, Inc. (USA) at 1:100; Anti-SOX2 antibody (cat no. 561469) from BD Pharmingen (USA) at 1:1000 and Anti-Nanog (cat no. 560109) from BD Pharmingen (USA) at 1:1000. Secondary antibodies are diluted 1:500 in 4% normal goat serum in 1×HBSS and incubated overnight at 4° C. followed by three room temperature washes and one hour room temperature incubation. Secondary antibodies are Goat anti-mouse Alexafluor-488 (cat no. A-11001) and Goat anti-mouse Alexafluor-568 (cat no. A-11004) from Life Technologies, USA. The mitochondrial stain TMRM (cat no. M 1406) from Sigma-Aldrich (USA) is used at 75 nM. Cells are stained by 20 minutes incubation in culture media in 5% $CO_2$ and 37° C.

Co-Localization of Blue Fluorescence to Organelles and Cellular Compartments

The constructs used to co-localize blue fluorescence with sub-cellular compartments and organelles are (RFP-KDEL) to mark Golgi, RFP-SKL to mark peroxisomes and RFP-GalT to mark the Endoplasmic reticulum. HuES7 cells are grown feeder-free and harvested on the day of the experiment ($0.1 \times 10^6$ cells/transfection). All transfections are done with the Neon Transfection System (Invitrogen, USA) using 10 µl tips. Fluorescence images of the cells are obtained after 48 hrs using the appropriate filters (see above) and analysed.

Spectrophotometry and Spectrofluorometry

Absorbance and fluorescence spectra of chloroform: methanol extracts of lipid bodies, serum (FBS) and serum replacement (KOSR) are obtained at room temperature using either a FluoroMax-3 spectrofluorimeter (Horiba Scientific, Japan) or a Cary-300 UV-Vis spectrophotometer (Agilent Technologies, USA) against a chloroform blank in a quartz cuvette The chloroform:methanol extracts are obtained from serum samples or KOSR extracted with an equal volume of chloroform:methanol (1:1) mixture by vortexing for 1 minute and then centrifuged (3000×g) for 10 minutes. The heavier chloroform:methanol fraction is removed, dried in a CentriVapand dissolved in 1 ml of chloroform and analysed.

Example 1

The instant example presents media used to propagate human and mouse pluripotent stem cells; media used to convert human pluripotent cells into primitive mouse embryonic stem cell like state; and normal mouse ES cells to an epiblast-like (like HuES cells) state.

Human Embryonic Stem Cell Standard Media (HuESM)—Standard Medium for Growing Human ES Cells:

Knockout DMEM (For ex.: Gibco by Life Technologies, catalog no. 10829018) with about 20% Knockout Serum Replacement (For ex.: Gibco by Life Technologies, catalog no. 10828-028), about 0.1 mM beta-mercaptoethanol (For ex.: Gibco, catalog no. 21985-023), about 1% of 100× Penicillin-Streptomycin (For ex.: Gibco by Life Technologies, catalog no. 15140-122), about 1% of 100× Non-Essential Amino Acids (For ex.: Gibco by Life Technologies, catalog no. 11140-050), about 1% of 100× GlutaMAX (For ex.: Gibco by Life Technologies, catalog no. 35050-061), about 5 ng/ml of basic Fibroblast Growth Factor—bFGF (For ex.: Peprotech, catalog no. 100-18B).

Human Embryonic Stem Cell Conversion Media (HuCM)—Conversion Medium—

Medium that favours the growth of the more primitive Mouse ES cell-like state:

Knockout DMEM, with about 15% Fetal Bovine Serum (For ex.: GIBCO, catalog no. 10270-106), about 0.1 mM beta-mercaptoethanol, about 1% of 100× Penicillin-Streptomycin, about 1% Non-Essential Amino Acids, about 1 mM GlutaMAX, about 1 ng/ml human LIF (For ex.: ProSpec, catalog no. CYT 644), about 10 ng/ml Interleukin-6 (For ex.: Sigma, catalog no. I1395), about 3 µM GSK-3α/β inhibitor BIO (For ex.: Sigma B 1686), about 1 µMAPK inhibitor PD98059 (For ex.: Sigma P215).

Mouse Embryonic Stem Cell Standard Media (MESM)—Standard Medium for Growing Mouse ES Cells:

Knockout DMEM with about 15% Fetal Bovine Serum, 0.1 Mm beta-mercaptoethanol, about 1% of 100× Penicillin-Streptomycin, about 1% of 100× Non-Essential Amino Acids, about 1% of 100× GlutaMAX and about 1000 units of Mouse LIF (For ex.: Millipore, ESGRO LIF).

Mouse Embryonic Stem Cell Conversion Media (MCM)—Conversion Medium—

Media used to convert normal mouse ES cells to an epiblast-like (like HuES cells) state:

Knockout DMEM with about 20% Knockout Serum—KOSR (For ex.: Gibco by Life Technologies, catalog no. 10828-028), about 0.1 mM beta-mercaptoethanol, about 1% of 100× Penicillin-Streptomycin, about 1% of 100× Non-Essential Amino Acids, about 1% of 100× GlutaMAX, about 15 mM Sodium dithionite added fresh (For ex.: Sigma), 10 ng/ml basic Fibroblast Growth Factor bFGF and about 1 ng/ml Activin (For ex.: Peprotech catalog no. 120-14).

Example 2: FACS Profile of Pluripotent Cells

The instant example provides a method for identifying and isolating human pluripotent stem cells from differentiated cells.

Cultures of human pluripotent stem cells are dissociated into single cells and sorted using a FACS machine based on endogenous blue fluorescence values.

1. Cultures of human pluripotent stem cells (HuES7 and HiPS cells) grown in standard human embryonic stem cell medium and on mitotically-inactivated Mouse Embryonic Fibroblasts (MEFs) as a feeder layer, are washed once with about IX PBS buffer. Alternatively pluripotent stem cells may be grown as feeder-free cultures.

The MEFS are mitotically inactivated mouse embryonic fibroblasts and are used as non-dividing substrate to grow the HuES or iPS cells. It can be avoided in some cases and cells can be grown on alternate substrates.

2. The cells are subjected to dissociation either by mechanical or enzymatic means. In the enzymatic method, approximately 300 µl of accutase (ESGRO Complete Accutase from Millipore, Catalog no. SF006) or Detachin or other cell detachment solution/other enzymatic cell dissociation reagent such as 300 µl of Tryp-LE (Invitrogen, USA) etcis added per 10 $cm^2$ surface area. The cells are then kept at about 37 degree Celsius for about 5 to 7 minutes, till the colonies begin to dissociate.

3. Standard HuES medium (KO-DMEM, 100 µM 2-Mercaptoethanol, 0.5% FBS, 10 nM nonessential amino acids, 100 mM L-glutamine and 5 ng/ml recombinant human basic fibroblast growth factor (bFGF)) 2 ml is added for every 300 µl of accutase and the culture is triturated to obtain a single cell suspension. Most of the MEFS remain attached to each other and are present as fibrous structure which is easily removed physically (for e.g, using a cell strainer—40 µm). Alternatively, 5 minutes of selective adhesion on fresh tissue culture dishes allows the removal of most MEFs.

4. The colonies are dissected mechanically using a syringe or StemProEZPassage Roller (Invitrogen) and then subsequently triturated to get single cells. This is done if enzymatic dissociation is to be avoided.

5. Cells are pelleted, about 200 g for about 5 minutes at temperature ranging from about 4° C. to about 37° C., preferably about 15° C. to about 30° C., more preferably at temperature of about 22° C. The cell pellet is resuspended in Sorting Medium (Same as standard HuES medium, except about 20% KOSR is replaced by about 0.5% FBS) in FACS tubes and kept on ice.

6. About 1 µg/µl of propidium iodide is added to the cell suspension and incubated for about 2 minutes at temperature ranging from about 4° C. to about 37° C., preferably about 15° C. to about 30° C., more preferably at temperature of about 22° C. before sorting to identify and separate dead cells.

Cells are sorted using a BD FACS Aria cell sorter, laser 375 nm near UV, Trigon detector for blue fluorescence and collected at 450/50 nm bandpass filter (DAPI channel); PMT voltage set at 350V for blue fluorescence); sheath flow pressure (20 pci); flow cell (100 µm). The sorter is then calibrated appropriately for standard parameters such as area scaling, laser delay and drop delay etc.

7. Sort analysis is initiated to define the appropriate gating to obtain live cells and to determine the distribution of blue fluorescence in the cell population.

Typical profiles of human pluripotent stem cells (HuES-7 and HiPSCs) show two distinct peaks which is characteristic of the culture. The means of the two peaks differ by at least an order of magnitude and the population with the higher fluorescence levels (on the right in FIG. 3c) is designated as the 'High Blue' and the population with the lower fluorescence levels (one on the left in FIG. 3c) is designated as 'Low Blue'. The distribution under each peak defines the quality and quantity of the cells. The instant disclosure's observations indicate that cells from colonies with good morphology and which have little or no patches of differentiating cells mainly fall within the 'High Blue' population. Conversely, colonies which exhibit differentiation consist of cells which mainly fall in the 'Low Blue' population.

FIG. 3 shows that lipid body-associated blue fluorescence is a pluripotency marker and aids in easy isolation and high throughput single cell propagation of HPSCs. (a) Lipid body associated blue fluorescence is co-expressed with pluripotency markers (OCT4, SOX2 and NANOG) in undifferentiated HuES7 cells. Differentiating regions identified by morphology (marked with red dashed line) shows absence of lipid body-associated blue fluorescence and pluripotency markers. (b) Scatter plots of mean fluorescence intensities of blue fluorescence vs pluripotency marker fluorescence (measured by marking equisized ROIs) shows positive correlation. (c) FACS analysis shows co-expression of blue fluorescence with OCT4 and SSEA4 markers. (d) Typical FACS scatter plots and histograms of undifferentiated HPSCs show a larger high blue population while differentiating cultures show the reverse. (e) Cell counts from high blue and low blue cell populations of undifferentiated and differentiating cultures. (f) Typical colonies from sorted high blue, low blue and unsorted cells. (g) Colony counts from high blue, low blue and unsorted cells from undifferentiated and differentiating cultures. (h) 'Low blue' cells are viable, have active mitochondria and do not have characteristic HuESC morphology. (i) Isolation and propagation of HuESCs from highly differentiated HuES cultures obtained by plating cells from 'high' blue population.

8. The sorted cells are collected at temperature ranging from about 4° C. to about 37° C., preferably about 15° C. to about 30° C., more preferably at temperature of about 22° C. in collection tubes containing standard human ES medium and propagated under conditions normally used.

9. To determine the pluripotent status of the 'High Blue' and 'Low Blue' population, equal numbers of cells from these populations are plated onto inactivated MEFs in standard human ES medium. An equal number of propidium iodide-negative sorted cells are plated to determine the advantage of sorting. The MEFS are non-dividing cells which are used as a surface on which pluripotent cells grow well, and they are termed as inactivated MEFs.

10. All cells which had been through the sorter are pelleted (to remove sheath fluid) and plated on fresh inactivated MEFs in standard HuES medium.

11. All plated cells are evaluated for colony formation and colony numbers are determined after day 7.

Example 3: Using Blue Fluorescence to Sort and Enrich for Human Pluripotent Stem Cells (HPSCs)

Since individual cells within a HPSC colony exhibit distinct but variable levels of blue fluorescence, its relationship to pluripotency and its utility to isolate undifferentiated cells from differentiating cells by FACS is examined.

On sorting cells using blue fluorescence (DAPI channel), HPSCs resolve into two distinct populations. The peak fluorescence intensities of the two populations differed by 10-fold and are labelled as 'high blue' and 'low blue' (FIG. 3d). Further, it is noticed that the relative proportion of cells with high blue fluorescence in the two populations characterize the 'pluripotent nature' of HPSCs. Cultures with largely undifferentiated colonies are characterized by a lower profile for the 'low blue' population and a higher profile for the 'high blue' population, while cultures with more differentiated colonies have the reverse profile (FIG. 3d). Furthermore, cultures with differentiating colonies have higher number of cells within the 'low blue' peak compared to undifferentiated cultures (FIG. 3e). The above observation is extended by plating equal number of cells (n=30,000) from 'high blue'; 'low blue' and an 'unsorted' population on conditioned MEF in typical media. The 'high blue' cell population always gives rise to larger numbers of colonies with the typical HuES-like morphology compared to the unsorted and 'low blue' populations (FIG. 3f,g). The unsorted cells also do better than the 'low blue' cells in terms of colony morphology and colony numbers (FIG. 3f, g). To rule out the possibility of massive cell death post-sorting in the 'low blue' population as the reason for the decreased colony numbers, propidium iodide-negative and sorted 'low blue' cells are plated and imaged after 4 days. Majority of the cells acquire a flattened morphology and stained positive for active mitochondria (Mitotracker deep red FM) and have un-fragmented nuclei (Hoechst) (FIG. 3h), suggesting that cells with 'low blue' fluorescent cells remain alive and represent the 'differentiating' fraction of cells in HPSC cultures. Repeated sorting/propagation of HPSC colonies (by FACS) do not alter the blue fluorescence profile suggesting that sorted cells continue to behave like regular HPSCs with some amount of differentiation always present (represented by cells within the 'low blue' peak).

In general, HPSC cultures with large percentages of differentiating cells are not known to survive multiple passages. In order to determine if such cultures can be rescued using blue fluorescence, differentiating HuES cultures are sorted and the cells with 'high blue' fluorescence are plated onto MEF feeders. Typical pluripotent colonies with discrete edges and uniform morphology are obtained by day 7 (FIG. 3i).

These results indicate that—(a) levels of lipid body-associated blue fluorescence correlate positively with pluripotency and self-renewal, (b) sorting for blue fluorescence facilitate high-throughput single cell propagation and (c) cells with 'low blue' fluorescence are the differentiated cells.

This method, therefore, presents significant advantages over existing protocols of isolating and propagating human pluripotent stem cells including single cells.

Example 4: Disappearance of Endogenous Fluorescence with Differentiation

The instant example presents a method for inducing human pluripotent stem cell to differentiate in order to observe that cultures of differentiated human pluripotent stem cells show decrease or absence of blue autofluorescence.

1. Human embryonic (HuES7)/induced pluripotent stem cells (induced from somatic cell lines LCL, ADF, NFF) are grown on a feeder layer of Mouse Embryonic Fibroblasts in standard HuES medium (with about 5 ng/ml bFGF), on regular tissue culture plastic.

2. To induce differentiation, human pluripotent stem cell colonies are grown in standard HuES medium in the absence of bFGF.

3. Within about 2-3 days, differentiated structures are seen amidst the colonies. Images are taken of colonies grown with bFGF and those grown in the absence of bFGF. (Phase contrast and blue fluorescence)

Images taken show the clear decrease/disappearance of lipid bodies in the differentiated cells with a concomitant decrease in blue autofluorescence (FIG. 3).

Example 5: Human Somatic Cells Acquire Blue Fluorescent Lipid Bodies Very Early During Reprogramming Lipid bodies with blue fluorescence are present in both human ES and HiPSC (human induced pluripotent stem cell) colonies (FIG. 1b and FIG. 4a) while in human somatic cells they are far fewer and not fluorescent. Therefore, the appearance of fluorescent lipid bodies in somatic cells that are being reprogrammed to become pluripotent is monitored. Cells from different somatic tissues i.e. human neonatal foreskin fibroblasts (NFF) and EBV-transformed adult lymphoblastoid cell lines (LCLs) are reprogrammed using the method of Okita et al. (2011). As early as 7-10 days post-transfection, clusters of cells begin to exhibit blue fluorescence while the surrounding MEF layer and somatic cells did not. Higher magnification shows the fluorescence to be associated with spherical bodies in the cytoplasm. Further, it is observed that these clusters of cells expand and give rise to HiPSC colonies and also retain the blue fluorescence as observed in stable HPSCs. The time of appearance of fluorescent lipid bodies vary with the type of somatic tissues. Blue fluorescent bodies are visible around 7-10 days post-transfection usually in the case of neonatal fibroblasts, while in case of LCLs the fluorescence appears around day 10-12 (FIG. 4). The cells that have fluorescent lipid bodies also express SSEA-4 (FIG. 5)—an established early reprogramming marker. The blue fluorescence distribution profiles of the newly formed HiPSCs are similar to those of stable HuES lines and are always higher (about 10-fold) than their somatic precursors. The lower levels of blue fluorescence observed as a single FACS peak in somatic cells can arise from NAD(P)H and other intrinsic fluorophores. These results indicate that the 'blue' fluorescence associated with lipid bodies serves as a reprogramming marker, and can aid in the identification of 'potential' reprogrammed cells.

Example 6: Blue Fluorescence in Mouse Embryonic Stem Cells is Mitochondrial in Origin Mouse embryonic stem cells show low levels of blue autofluorescence. The instant example presents a method to show the localization of blue autofluorescence to the mitochondria in mouse embryonic stem cells by, employing a fluorescent red dye that stains mitochondria in live cells.

1. Mouse ES D3 cells are grown on feeder layer of MEFs in standard Mouse ES medium with about 15% Fetal Bovine Serum and mouse LIF, on regular tissue culture plastic.

2. Mouse ES colonies are plated on coverslip dishes with MEFs to enable high magnification (60×) imaging.

3. About 100 nM of MitoTracker Red (Invitrogen) is added to the medium and incubated at about 37 degrees for about 45 minutes to about 1 hour. MitoTracker Red (Mito-Red) is a red-fluorescent dye that stains mitochondria in live cells 4. After about 1 hour, the medium with MitoTracker Red is washed off and the colonies are imaged in fresh medium.

Fluorescence images of blue autofluorescence and red fluorescence from the dye are acquired and colocalisation is observed. This indicates that the blue autofluorescence in Mouse ES cells comes from mitochondria (FIG. 6).

Example 7: Human Embryonic Cell to Mouse Embryonic Cell-Like State Conversion

The instant example explains a method for culturing human embryonic stem cells HuES7 in human embryonic stem cell conversion medium (HuCM), to convert them to more primitive/naïve state, which show a significant decrease in the number of blue fluorescent lipid bodies (FIG. 6).

1. Human embryonic/induced pluripotent stem cells are grown on a feeder layer of Mouse Embryonic Fibroblasts in standard HuES medium (with about 5 ng/ml bFGF), on regular tissue culture plastic.

2. Human pluripotent stem cell colonies are plated on coverslip dishes on MEFs to enable high magnification (60×) imaging.

3. The media used to convert is modified slightly from an earlier protocol (Hanna, J. et al. Human embryonic stem cells with biological and epigenetic characteristics similar to those of mouse ESCs. *Proceedings of the National Academy of Sciences of the United States of America* 107, 9222-7 (2010) by—(a) substituting DMEM/F12 with KO-DMEM and (b) substituting the small molecule GSK3β inhibitor—CHIR99021 with another GSK3β inhibitor—BIO (Sigma-Aldrich, USA cat. No. B1686). Media is changed daily and the colony morphology, disappearance of lipid bodies and change in corresponding fluorescence are monitored.

4. Colonies are grown in the conversion medium for about 7-10 days. The human ES cells which grow in monolayers as flat circular colonies with visible internal lipid bodies which exhibit blue fluorescence show a decrease in the lipid bodies which disappear completely in about 7 to 10 days in culture.

Example 8: Mouse Embryonic Stem Cell to Mouse Epiblast (Human Embryonic Stem Cell-Like) State Conversion The instant example presents a method for converting mouse embryonic stem cells to mouse epiblast-like cells which show a significant increase in the number of lipid bodies emitting blue fluorescence (FIG. 6).
1. To convert mES cells to an EpiSC state i.e. 'naive' to 'primed' state, mESR1 and D3 cells are grown in typical human ES medium with 2000 units/ml LIF (Millipore, USA, cat. no ESG1107) and 10 ng/ml bFGF on 0.1% gelatin-coated glass coverslip dishes.
2. Glass cover slips are washed with 100% ethanol, sterilized with UV for 3 hours and coated with 0.1% gelatin (300 Bloom) (Sigma-Aldrich, USA, cat. No. G3500) in 1×PBS.
3. Hypoxic conditions are induced by adding 1.5 mM sodium dithionite (Sigma-Aldrich, USA, cat. no. 157953) to the media which is replaced daily.
4. The cells are closely monitored for change in morphology and for the appearance of lipid bodies along with the associated fluorescence characteristics.

Example 9: Blue Fluorescent Lipid Bodies are Associated with the 'Primed' or 'Epiblast-Like' State To ascertain whether the fluorescent lipid bodies are specifically associated with the 'primed' state, mouse ES cells are examined. Among the many differences between human and mouse pluripotent stem cells, the mouse cells are believed to represent a 'naive' state while the human cells represent a slightly later developmental stage termed the 'primed' or 'epiblast' state. Mouse ESC colonies grown in 20% KOSR ES cell media show very faint blue fluorescence compared to HPSC colonies (FIG. 6). Higher magnification images of BODIPY®493/503-stained mES cells show very few lipid bodies, almost always around the edges of the colonies, and furthermore, these are not fluorescent in blue (FIG. 6). Analysis of subcellular compartments of mES cells show that the endogenous faint blue fluorescence in mES cells co-localize with mitochondria, stain with TMRM (a mitochondria-specific dye) (FIG. 6$d$) ($R^2$=0.93). This is unlike human pluripotent cells where high blue fluorescence is excluded from the mitochondria and present in lipid bodies (FIG. 1). Sorting of mouse ES cells present a single population with lower blue fluorescence than human pluripotent stem cells. These results suggest that the sources of the blue fluorescence observed in mESCs and HPSCs are different and that the blue fluorescent lipid bodies may be associated with the 'primed' or 'epiblast-like' state.

Thus this association is explored by shifting pluripotent stem cells from the 'primed' state to the 'naive' state and vice-versa. HuES cells are cultured in media that promotes their conversion to the 'naive' state. Within 48 hours the HuES cells show a significant decrease in blue fluorescence along with corresponding decrease in the number of lipid bodies (FIG. 6$f,h$). Similarly, mES cells, are cultured in media that triggers their conversion to the 'primed' state and the cells begin to acquire fluorescent lipid bodies (FIG. 6$g,i$) strengthening the association of the epiblast-like state with blue fluorescent lipid bodies. Cells grown in 'conversion' media continue to express OCT4 and are not stained with Propidium iodide (PI) confirming their pluripotent state and viability (FIG. 7$a,b$—middle and lower panel). The HPSCs and mESCs grown in their respective 'typical' media as well as in their 'conversion' media are also subjected to FACS analysis. The analysis shows that there are significant changes in the mean blue fluorescence intensity and profile in both the cell lines in the expected directions. These results clearly show that the lipid body associated blue fluorescence could be linked to the specific cell state i.e. the epiblast-like cells.

Example 10: Blue Fluorescent Lipid Bodies are Absent in Mouse Inner Cell Mass, Mark Many Cells of the Mouse Epiblast and are Also Present in Mouse Epiblast-Like Stem Cells To determine if the blue fluorescent lipid bodies are also present in vivo and mark the 'primed' or 'epiblast-like' cells. Timed pregnant female mice—CF1 strain are obtained from the NCBS Animal Facility and the mouse embryos are dissected out at DPC (Days post Coitus) 6.5, a developmental stage from which mouse epiblast stem cells (mEpiSCs) are derived. The epiblast region of the embryo exhibit punctate blue fluorescence which is also stained by BODIPY®493/503 (FIG. 8). These results suggest that the blue fluorescent lipid bodies observed in HPSCs as well as in the mouse epiblast are similar and may be characteristic of the 'primed' or 'epiblast-like' pluripotent stem cells.

To determine if the blue fluorescent lipid bodies are also present in vivo and specifically mark the 'primed' or 'epiblast-like' cells, mouse embryos are examined at DPC 3.5—to evaluate mouse inner cell mass (ICM), and DPC 6.5, a developmental stage from which mouse epiblast stem cells (mEpiSCs) are derived. Confocal images of DPC 3.5 embryos show very few BODIPY® 493/503 stained lipid bodies, and these are not fluorescent in the blue region and do not localise to the ICM region of the embryo (FIG. 8). On the other hand, the DPC 6.5 embryo exhibit intense blue fluorescence overall. The distal epiblast region of the DPC 6.5 embryo that gives rise to EpiSC show blue fluorescent puncta which are also stained by BODIPY®493/503 (FIG. 8). These results suggest that the blue fluorescent lipid bodies may be a marker for the epiblast state and these are observed in HPSCs as well as in the mouse epiblast, and may be characteristic of the 'primed' or 'epiblast-like' pluripotent state.

Staining of Lipid Bodies in Mouse Embryos (E6.5) and Generation of Mouse EpiSCs

Post-implantation embryos (E6.5) are isolated from CF1 mice using method described by Shea, K. & Geijsen, N. Dissection of 6.5 dpc mouse embryos. *Journal of visualized experiments: JoVE* 160 (2007). doi:10.3791/160. The embryos are imaged as described earlier for blue fluorescence using a Nikon Eclipse TE2000-E-PFS microscope. The embryos are also stained with BODIPY® 493/503 as described before to identify lipid bodies and determine their level of co-localization with the blue fluorescence.

Mouse EpiSC cells are derived from E6.5 embryos. The ectoplacental cone is separated from the embryos and individual egg cylinders are gently triturated (using a 20 μl micropipette) resulting in small clumps and plated on mitotically inactivated MEFs in mEpiSC media (typical HuES media supplemented with 15% KOSR and 5% FBS with 10 ng/ml bFGF and no LIF). Flattened out colonies are observed by 24-48 hrs. The colonies are mechanically dissected into small pieces and propagated once every 3-4 days under the same culture conditions. The colony morphology and presence of lipid body-associated blue fluorescence is observed and evaluated at each passage.

Cells from the mouse embryos (E6.5) in EpiSC-specific media (KOSR 15% and FBS 5% with bFGF) are cultured and the 'epiblast-like' colonies that result retain the fluorescent lipid bodies (FIG. 8). These results suggest that fluorescent lipid bodies are a property characteristic of the 'epiblast-like' state of pluripotent stem cells and differentiates them from cells in the 'naive' state.

Example 11: Retention of Autofluorescence in Paraformaldehyde Fixed Colonies

The instant example presents a method to show the retention of endogenous blue fluorescence within the lipid bodies even in cells fixed with paraformaldehyde.

1. Human embryonic/induced pluripotent stem cells are grown on a feeder layer of Mouse Embryonic Fibroblasts in standard HuES medium (with about 5 ng/ml bFGF), on regular tissue culture plastic.
2. Colonies are imaged before addition of 4% paraformaldehyde (PFA) for blue autofluorescence using standard fluorescence microscope (specifications mentioned earlier).
3. 4% PFA is added to these colonies and they are imaged for blue autofluorescence after fixation. Blue autofluorescence is observed before and after 4% PFA fixation (FIG. 3).

Example 12: Immunofluorescence with Oct-4 Antibody

Human pluripotent stem cell colonies (HPSC) often show signs of differentiation, which are strikingly apparent as altered morphology, mostly noticed at the periphery and occasionally at their center. Pluripotency markers like Oct-4, Sox2, Nanog are routinely used to determine the differentiation status of HPSCs but require cells to be fixed and immunostained or engineered to report their expression.

Oct-4, Sox2, Nanog are well established markers and drivers of pluripotency. The endogenous blue fluorescence levels correlate with Oct-4, Sox2 and Nanog expression and the instant example describes a method for determining levels of Oct-4, Sox2 and Nanog proteins in pluripotent stem cells by immunofluorescence, without having to genetically modify the cells, to show the positive correlation with levels of blue fluorescence.

1. Human embryonic/induced pluripotent stem cells are grown on a feeder layer of Mouse Embryonic Fibroblasts in standard HuES medium with about 5 ng/ml basic fibroblast growth factor (bFGF), on regular tissue culture plastic.
2. Human pluripotent stem cell colonies are plated on coverslip dishes on MEFs to enable high magnification (60×) imaging. Prior to staining, these cells are washed thrice with about 1× HBSS with $Ca^{2+}$ and $Mg^{2+}$.
3. About 4% Paraformaldehyde (PFA) is added to the colonies and kept at temperature ranging from about 4° C. to about 28° C. for about 20 minutes to fix the cells.
4. PFA is removed and colonies are washed with Rinse Buffer (HBSS with about 0.1% Tween-20) twice for about 10 minutes each.
5. Permeabilisation Buffer (HBSS with about 0.1% Triton) is added for about 10 minutes.
6. Colonies are then washed with Rinse Buffer again, twice for about 10 minutes each.
7. Blocking is done using about 4% Normal Goat Serum (NGS) for about 30 minutes.
8. The primary antibody (anti mouse Oct 3/4 from Santa Cruz, Catalog no. (C-10): sc-5279) is added at 1 in 300 dilution, diluted in 1×HBSS and colonies are kept at about 4 degrees overnight.
9. After overnight (about 12 to 16 hours) incubation, colonies are washed with Rinse Buffer three times, about 10 minutes each.
10. Secondary antibody (Goat anti mouse Alexa Fluor 488 dye from Invitrogen) is added at 1 in 500 dilution (diluted in 1×HBSS) for about an hour.
11. After an hour, the secondary antibody is washed off with Rinse Buffer (three times, 10 minutes each).
12. The colonies are imaged for blue autofluorescence and Oct 4, Sox2 or Nanog staining using Nikon TE Eclipse inverted microscope (10× and 60× magnification).
13. The resultant images are analyzed using ImageJ software and fluorescence values in discrete areas are compared.

It is observed that spontaneously differentiating human pluripotent stem cell colonies, do not exhibit blue autofluorescence and cells in these areas do not express or have very low levels of Oct-4, Sox2 and Nanog in their nuclei (FIG. 3).

Examination of HPSC cultures show that cells which stain positive for pluripotency markers also express blue fluorescence at similar levels (FIG. 3). In areas within colonies, where cells look differentiated, the fluorescent lipid bodies had either disappeared or had decreased with a corresponding absence/decrease in fluorescence levels of OCT4, SOX2 and NANOG levels. Mean fluorescence intensity values from cells expressing both blue fluorescence and pluripotency markers result in a tight linear fit—OCT4 ($R^2$ (correlation coefficient)=0.9) SOX2 ($R^2$=0.9) and NANOG ($R^2$=0.83) (FIG. 3b). It is further demonstrated by FACS analysis that cells with blue fluorescence always co-express SSEA-4 and TRA-1-60 antigens (surface pluripotency markers) (FIG. 3). These results suggest that in HPSCs blue fluorescence and pluripotency markers are tightly correlated and thus the blue fluorescent lipid bodies serve as an internal marker for pluripotency.

Example 13: Oil Red Staining Protocol

The instant example provides a method for performing Oil red staining to confirm that the bodies that emit blue autofluorescence are indeed lipid bodies.

1. Human embryonic/induced pluripotent stem cells are grown on a feeder layer of Mouse Embryonic Fibroblasts (MEFs) in standard HuES medium with about 5 ng/ml basic fibroblast growth factor (bFGF), on regular tissue culture plastic.
2. Human pluripotent stem cell colonies are plated on coverslip dishes on MEFs to enable both high magnification (60×) and low magnification (4×) imaging. Prior to staining, these cells are washed with about 1×PBS.
3. About 1 ml of about 10% formalin is added and the cells are incubated for about 30 to 60 minutes at a temperature range of 4° C.-37° C.
4. Oil Red O stock solution is made by dissolving about 300 mg of Oil Red O (Catalog no. 09755, from Sigma) in about 100 ml of about 99% isopropanol. This stock solution is stored at a temperature ranging from about 21° C. to about 28° C.
5. For making the working stock, 3 parts of Oil Red O stock solution is mixed with 2 parts of distilled water and allowed to sit at a temperature ranging from about 21° C. to about 28° C. for about 10 minutes. (This working stock is only stable for 2 hours).

6. The working solution is filtered through a Whatman filter paper before use.

7. The formalin is removed after and the colonies are rinsed with about 2 ml of sterile water.

8. About 1 ml of about 60% isopropanol is added to each dish and kept for about 5 minutes.

9. Isopropanol is removed and the filtered Oil Red O working stock solution is added slowly and the dish is kept on the shaker for about 5 minutes.

10. The colonies are washed with water three times before imaging.

Imaging is done under bright field or fluorescence. (Excitation—530-560 nm, Dichroic 570 Long Pass, Emission—590-650 nm). To stain with BODIPY® 493/503 (Invitrogen, USA) (cat no. D-3922) a stock of the dye at 1 mg/ml in methanol is diluted to 1 ug/ml in culture media and the cells are incubated for 15 minutes and washed thrice with 1×PBS and then imaged (Excitation—500 nm/20, Dichroic 535 nm/30, Emission 515 Long Pass).

It is observed that the fluorescent cytoplasmic bodies in the human pluripotent stem cells do not localize with ER, Golgi or mitochondrial markers, but stain with oil red, which identify them as lipid bodies (FIG. 2).

FIG. 2 shows the endogenous blue fluorescence in human pluripotent stem cells which is punctuate and localized to lipid bodies. (a) HPSC cultures (HuES7, NFF_iPSCs, ADF_iPSCs and LCL_iPSCs) show numerous lipid bodies (positive Oil RedO staining) (b) Oil Red O positive lipid bodies in human neonatal (NFF) and mouse embryonic (MEF) fibroblasts do not exhibit blue fluorescence and are not as prominent as in HPSCs. (c) Mesenchymal stem cells (MSCs) derived from human bone marrow and placenta do not exhibit blue fluorescence. (d) The blue fluorescence is significantly higher in HPSCs cultures compared to somatic cells. Mean fluorescence intensities are in arbitrary units (n=3, multiple colonies from three independent cultures for each cell type). (e) Neurons derived from HuES7 do not exhibit blue fluorescence. (f) The blue fluorescent lipid bodies present in HuES7 do not co-localize with endoplasmic reticulum, (ER—upper panel), Golgi apparatus (middle panel) or peroxisomes (lower panel).

Example 14: Blue Fluorescence in Retinyl Esters Sequestered in Cytoplasmic Lipid Bodies To determine the source of the blue fluorescence, lipid bodies are first isolated from human embryonic stem cells through differential sucrose gradient centrifugation.

Isolation and Characterization of Lipid Bodies from HuES7 Stem Cells

Lipid bodies are isolated using a density gradient ultracentrifugation method as detailed below 300 colonies are scraped and re-suspended in 2 ml of 2M sucrose solution in 10 mM Tris-1 mM EDTA buffer pH 7.4. The cell suspension is vortexed four times for 30 seconds each with 2 minute incubations on ice between each vortex. The cells suspension is then passed four times through a 26 G needle. 2 ml each of 0.27M and 0.135M sucrose in Tris-EDTA buffer are layered sequentially onto the cell suspension in clear ultracentrifuge tubes (Beckman (USA) Part No. 344060) and centrifuged at 1,50,000×g in a Beckman SW 40 Ti rotor for 1 hour and allowed to decelerate without braking. The topmost layer containing the lipid bodies is collected and stored at −20° C. till use.

Isolated lipid bodies remain fluorescent (FIG. 10) and the fluorescence partitions into the organic phase on extraction with chloroform:methanol (3:1). This indicates that the fluorophore present in lipid bodies is hydrophobic and unlikely to be a charged molecule. The chloroform:methanol extract is found to have absorbance and fluorescence characteristics i.e. excitation and emission profiles very similar to vitamin A (retinol or retinyl esters such as retinylpalmitate or retinyloleate). The fluorescence spectra of the chloroform:methanol extract and retinylpalmitate are identical (FIG. 10). The components of the chloroform:methanol extract are then resolved through reverse phase HPLC and compared with retinoid compound standards (retinylpalmitate, retinol and retinyl acetate).

Reverse Phase HPLC and Identification of Retinyl Ester

Isolated lipid bodies are extracted with an equal amount of 1:1 (chloroform:methanol mixture) by vortexing at room temperature for 1 minute followed by flash centrifugation. The lower heavier organic phase is collected and dried in a CentriVap console (Labconco, USA). The dried $CHCl_3$:MeOH extract is dissolved in 50 μl of acetonitrile and separated on a C-18 reverse phase HPLC column (Zorbax—C-18 column, Agilent technologies). The oven temperature is kept at 40° C. The solvent/mobile phase is 1:1:1:1 (ethanol:methanol:acetonitrile:isopropanol). The standards used are Retinyl Palmitate (Cat. No. R3375), Retinyl Acetate (Cat No. R7882) and Retinol (Cat No. R7632) from Sigma-Aldrich, USA. 800 ng of retinyl palmitate and 200 ng each of retinyl acetate and retinol are used per injection.

The retention time of the primary/main peak of the chloroform:methanol extract coincides with that of the retinyl palmitate standard at 18.65 minutes and is substantially different from those of retinol and retinyl acetate (6.65 and 7.33 minutes respectively) (FIG. 10). This indicates that the fluorescence emanating from the lipid bodies is largely from retinyl esters such as retinyl palmitate or a retinoid very similar to it, such as retinyl oleate. A plausible reason for the sequestration of vitamin A by lipid bodies in HPSCs may be for storage and later use as retinoic acid for differentiation. The storage of retinoids as esters in lipid bodies will prevent oxidation and conversion to retinoic acid, a powerful differentiation signal for pluripotent stem cells.

Example 15: Increase in Blue Fluorescence Upon Addition of Retinol or Retinyl Ester to Culture Media Animal cells are unable to synthesize vitamin A, but acquire it from carotenoids present in plants and through the food chain. For cells in culture, vitamin A is available from the serum in media largely as retinol. Retinol is taken up by cells and converted to retinyl esters such as palmitate and oleate or oxidized to retinal and retinoic acid. The presence of retinol is examined in typical HuES media which contains Knockout Serum Replacement (KOSR) or ES cell-certified serum. Media and serum samples are extracted with chloroform:methanol and resolved by reverse phase HPLC. KOSR and serum extracts are found to be fluorescent and contain retinol with retention times that matched the retinol standard at 6.65 minutes.

To determine if HPSCs can take up retinyl esters directly from the media and to prove that the blue fluorescence is directly correlated with retinyl ester levels, cells are grown on MEF feeder cells in typical media containing 20% KOSR and supplemented with retinyl palmitate at various concentrations (2-10 µM). After 24 hours, a dose-dependent saturable increase in the mean blue fluorescence intensity is observed in the lipid bodies (FIG. 10). The increase in fluorescence intensities is also found to be confined to the lipid bodies. It is observed that mouse embryonic stem cells show practically no increase in retinoid-associated fluorescence even after 48 hours in media with retinol (FIG. 9). This shows that supplementing the culture media with retinol or retinyl palmitate causes a dose-dependent increase in the blue fluorescence in the HPSCs emanating from the lipid bodies indicating retinoid uptake from the culture media and its sequestration within lipid bodies.

Example 16: Sequestration of Exogenously Provided Vitamin A in Lipid Bodies Unique to Pluripotent Stem Cells in the 'Primed' or 'Epiblast-Like' State HPSCs routinely cultured in typical media (Knockout DMEM, 20% KOSR with bFGF) have blue fluorescent lipid bodies. Since both human and mouse pluripotent stem cells are routinely cultured in media containing vitamin A (retinol), the presence of fluorescent lipid bodies in 'primed' HPSCs but not in 'naïve' mouse embryonic stem cells suggests that 'naïve' cells do not take up retinol but 'primed' cells do. This is also strongly suggested by the appearance of lipid bodies that are fluorescent in mouse 'epiblast-like' stem cells and the decrease in fluorescent lipid bodies in 'naïve' human pluripotent cells.

In addition to this, cultures of HuES cells in Essential 8 (E8) media (Invitrogen, USA)—a recently available, chemically-defined serum-free media for HPSC cultures that does not contain any vitamin A are examined. HuES cells cultured in E8 media show a rapid decrease in lipid bodies along with associated fluorescence in 24 hours, and the lipid bodies are completely absent by 72 hours (FIG. 10). Subsequently, addition of retinol (10 µM) to these cultures result in the re-appearance of fluorescent lipid bodies (FIG. 10). Together with the previously described results, this suggests that 'primed' pluripotent stem cells can take up retinoids, and that retinol can induce lipid bodies that sequester retinyl esters. A possible reason could be the differential expression of proteins involved in retinoid uptake and metabolism between the two states/cell types.

Therefore, these lipid bodies that sequester retinoids mark the 'epiblast-like' state in vivo and in vitro and may serve as a useful marker to distinguish between 'naïve' and 'primed' pluripotent stem cells. In other words, retinyl ester containing lipid bodies serve as marker for 'primed' or 'epiblast-like' pluripotent stem cells.

ADVANTAGES & APPLICATIONS

The instant disclosure describes a method which easily lends itself to high throughput propagation of human pluripotent stem cells employing FACS which involves obtaining single cells, sorting and propagating the single cells. The instant method also demonstrates the sorting and propagation of single human pluripotent cells.

The variability that is often associated with antibody labeling is also avoided.

Levels of the endogenous autofluorescence are easily quantified.

Being a robust endogenous marker, it provides a very stable and quantifiable platform.

The present method is used to identify and isolate human pluripotent stem cells from their differentiated counterparts rapidly and efficiently without modifying the cells in any manner, since it uses endogenous fluorescence. Therefore it does not require external labeling.

It is used for small scale and large scale cultures equally well. It lends itself to obtaining homogenous cell populations.

Since the fluorescence appears very early in the process of reprogramming (day 10 in case of reprogramming human lymphoblastoid cells and day 7 in case of human neonatal fibroblast cells) and is also retained once iPS colonies form—it can be used to track the efficiency of conversion for e.g. it is used to monitor/quantitate/or assay efficiency of conversion of various somatic cell types toward pluripotency under different experimental conditions. For e.g. it serves in high throughput assays to identify/define reprogramming conditions such as media constituents or analyse the biochemical processes involved.

It is also used to remove pluripotent stemteratoma forming cells i.e. pluripotent cells from differentiating/differentiated cells prior to transplantation.

It lends itself to high-throughput assays to monitor differentiation/loss of pluripotency and analyse the biochemical processes involved.

TABLE 1 shows the differential expression of protein involved in retinoid uptake and metabolism between human embryonic stem cell and mouse embryonic stem cell.

| SYMBOL | GENE NAME | HuES7 (U133A; Enver et al., 2005) http://amazonia.transcriptome.eu/ | mES (GSM87830_MoES.C5 http://www.ncbi.nlm.nih.gov/ |
|---|---|---|---|
| CRABP1 | cellular retinoic acid binding protein 1 | 819.6 | 378 |
| CRABP2 | cellular retinoic acid binding protein 2 | 1506.1 | 0 |
| RARA | retinoic acid receptor, alpha | 87 | 86 |
| RARG | retinoic acid receptor, gamma | 152.6 | 131 |
| RARRES2 | retinoic acid receptor responder (tazarotene induced) 2 | 632.2 | 0 |
| RBP1 | retinol binding protein 1, cellular | 315.3 | 5 |
| RBP7 | retinol binding protein 7, cellular | 55.7* | 94 |
| RETSAT | retinol saturase (all-trans-retinol 13,14-reductase) | 184.5 | 0 |
| RXRA | retinoid X receptor, alpha | 323 | 66 |
| STRA6 | Stimulated by retinoic acid gene 6 homolog | 251.3 | 0 |
| RALDH | retinal dehydrogensse | 13.5 | 2 |
| SOCS3 | Suppressor of cytokine signaling 3 | 65 | 95 |
| LRAT | Lecithin retinol acetyltransferase | 20.8 | 0 |

It is used to isolate mouse pluripotent cells which are epiblast-like pluripotent cells and is also used to get human pluripotent cells that are more 'naïve' like mouse ES cells.

To isolate and propagate epiblast stem cells from mouse and the more 'naive' like state from human ES and iPS cells.

To sort for cells with higher levels of blue fluorescence and propagate them repeatedly, particularly human iPS cells. This results in iPS cells that are closer in phenotype to human ES cells and possess a more uniform pluripotency-associated gene expression pattern further from their somatic ancestors.

Also if during the process of redifferentiation, blue cells are isolated very early during reprogramming, the reprogramming time may be shortened and the labour and expense involved is thus decreased.

Method of identification is coupled to dual photon/multiphoton FACS or other technology not utilising UV or near UV wavelength light for identification and isolation of pluripotent stem cells.

We claim:

1. A method for identifying primed mouse or human pluripotent stem cell(s) in a culture and optionally isolating the primed mouse or the human pluripotent stem cell(s) from the culture, said method comprising acts of:
    a) subjecting the culture to excitation at wavelength ranging from about 275 nm to about 410 nm for obtaining endogenous blue fluorescence emission from a retinyl ester containing lipid body present within the pluripotent stem cell(s); and
    b) measuring intensity of the blue fluorescence emission from the retinyl ester containing lipid body to identify the primed mouse or the human pluripotent stem cell(s) in the culture;
    c) optionally sorting the culture to isolate the primed mouse or the human pluripotent stem cell(s) from the culture.

2. The method as claimed in claim 1, wherein the culture comprises cells selected from a group comprising non-differentiating stem cell(s), differentiating stem cell(s), differentiated stem cell(s), stem cell(s) having pluripotency and a combination thereof.

3. The method as claimed in claim 1, wherein the excitation is from a single photon source or a multiphoton source.

4. The method as claimed in 1, wherein the intensity of endogenous blue fluorescence emission is at a wavelength ranging from about 410 nm to about 550 nm.

5. The method as claimed in claim 4, wherein the endogenous blue fluorescence emission is detected using a technique selected from a group comprising fluorescence microscopy, epifluorescence microscopy, dual microscopy, multiphoton microscopy and a combination thereof.

6. The method as claimed in claim 1, wherein the pluripotent stem cell(s) is selected from a group comprising a human embryonic stem cell (HuESC), a human induced pluripotent stem cell (HiPSCs), a mouse epiblast pluripotent stem cell (mEpiSC) and a combination thereof.

7. The method as claimed in claim 6, wherein the human induced pluripotent stem cell (HiPSCs) is selected from a group comprising a human lymphoblastoid induced pluripotent stem cell (LCL iPSCs), a human neonatal foreskin fibroblast induced pluripotent stem cell (NFF iPSCs), a adult dermal fibroblast induced pluripotent stem cell (ADF iPSCs) and a combination thereof.

8. The method as claimed in claim 1, wherein the sorting is carried out by Fluorescence Activated Cell Sorting technique.

9. The method as claimed in claim 1, wherein the blue fluorescence arises from retinoids within the lipid bodies of the pluripotent stem cell(s).

10. The method as claimed in claim 1, wherein the isolated pluripotent stem cell(s) is employed for propagation.

* * * * *